US010799679B2

(12) United States Patent
Roberts et al.

(10) Patent No.: US 10,799,679 B2
(45) Date of Patent: Oct. 13, 2020

(54) SECUREMENT DEVICE AND ASSEMBLY

(71) Applicant: Medline Industries, Inc., Northfield, IL (US)

(72) Inventors: Derek Roberts, Chicago, IL (US); Sarah Dickinson, Chicago, IL (US); Michael Turturro, Arlington Heights, IL (US); Lindsay Hilbelink, Salem, WI (US); Paige Wexler, Highland Park, IL (US)

(73) Assignee: Medline Industries, Inc., Northfield, IL (US)

( * ) Notice: Subject to any disclaimer, the term of this patent is extended or adjusted under 35 U.S.C. 154(b) by 253 days.

(21) Appl. No.: 15/830,930

(22) Filed: Dec. 4, 2017

(65) Prior Publication Data

US 2018/0154117 A1 Jun. 7, 2018

Related U.S. Application Data

(60) Provisional application No. 62/430,182, filed on Dec. 5, 2016.

(51) Int. Cl.
*A61M 25/02* (2006.01)

(52) U.S. Cl.
CPC ..... *A61M 25/02* (2013.01); *A61M 2025/0206* (2013.01); *A61M 2025/028* (2013.01); *A61M 2025/0253* (2013.01)

(58) Field of Classification Search
CPC ............ A61M 25/02; A61M 2025/028; A61M 2025/0253; A61M 2025/0206
See application file for complete search history.

(56) References Cited

U.S. PATENT DOCUMENTS

| D79,089 | S | 7/1929 | Kostenbader | |
|---|---|---|---|---|
| 4,397,647 | A * | 8/1983 | Gordon | A61M 25/02 128/DIG. 26 |
| D276,272 | S | 11/1984 | Weissenburger | |
| D331,462 | S | 12/1992 | Kraus | |
| D356,161 | S | 3/1995 | Peterson | |
| 5,549,567 | A * | 8/1996 | Wolman | A61M 25/02 604/179 |
| 5,693,032 | A | 12/1997 | Bierman | |

(Continued)

OTHER PUBLICATIONS

PCT Search Report and Written Opinion from International Application No. PCT/US2017/064648 dated Mar. 22, 2018; 13 pages.

(Continued)

*Primary Examiner* — Amber R Stiles
(74) *Attorney, Agent, or Firm* — Fitch, Even, Tabin & Flannery LLP

(57) ABSTRACT

In one aspect, a catheter securement device comprises a body portion having an upper surface and a lower surface, the body portion having a pocket that comprises a substantially tubular channel, the channel being open at the upper surface, the pocket further including a port cavity in communication with the channel. The securement device further comprises a strap portion movable between a fully closed position and a range of open positions. The strap portion at least partially covers the pocket when in a closed position thereby closing the channel at the upper surface. The strap portion allows access to the channel when in an open position.

25 Claims, 23 Drawing Sheets

(56) References Cited

U.S. PATENT DOCUMENTS

| | | | |
|---|---|---|---|
| 5,702,371 A * | 12/1997 | Bierman | A61M 25/02 128/DIG. 26 |
| D427,307 S | 6/2000 | Guala | |
| D431,650 S | 10/2000 | Guala | |
| 6,361,523 B1 | 3/2002 | Bierman | |
| 6,413,240 B1 | 7/2002 | Bierman | |
| 6,428,515 B1 | 8/2002 | Bierman | |
| 6,572,588 B1 | 6/2003 | Bierman | |
| 6,582,403 B1 | 6/2003 | Bierman | |
| 6,663,600 B2 | 12/2003 | Bierman | |
| 6,673,046 B2 | 1/2004 | Bierman | |
| 6,770,055 B2 | 8/2004 | Bierman | |
| 6,972,003 B2 | 12/2005 | Bierman | |
| 7,014,627 B2 | 3/2006 | Bierman | |
| 7,018,362 B2 | 3/2006 | Bierman | |
| 7,223,256 B2 | 5/2007 | Bierman | |
| D557,410 S | 12/2007 | Hitchcock | |
| 7,491,190 B2 | 2/2009 | Bierman | |
| 7,520,870 B2 | 4/2009 | Bierman | |
| 7,563,251 B2 | 7/2009 | Bierman | |
| D597,666 S | 8/2009 | George | |
| 7,635,355 B2 | 12/2009 | Bierman | |
| D618,792 S | 6/2010 | Bierman | |
| D619,711 S | 7/2010 | Lombardo | |
| 7,762,991 B2 | 7/2010 | Bierman | |
| 7,785,295 B2 | 8/2010 | Bierman | |
| 7,799,001 B2 | 9/2010 | Bierman | |
| 7,837,655 B2 | 11/2010 | Bierman | |
| 7,863,610 B2 | 1/2011 | Rajendran | |
| D637,712 S | 5/2011 | Chau | |
| 7,935,083 B2 | 5/2011 | Bierman | |
| 7,955,307 B2 | 6/2011 | Bierman | |
| 8,105,289 B2 | 1/2012 | Bierman | |
| D655,407 S | 3/2012 | Chuck | |
| D672,004 S | 12/2012 | Stracener | |
| D680,857 S | 4/2013 | Rumpel | |
| D687,537 S | 8/2013 | Au | |
| 8,585,655 B2 | 11/2013 | Bierman | |
| 8,636,699 B2 | 1/2014 | Russo | |
| 8,689,798 B2 | 4/2014 | Sabin | |
| D706,083 S | 6/2014 | Kyuba | |
| D712,024 S | 8/2014 | Au | |
| D747,636 S | 1/2016 | Maher | |
| D764,057 S | 8/2016 | Schaffner | |
| D767,761 S | 9/2016 | Babb | |
| D768,849 S | 10/2016 | Eisenberg | |
| D775,352 S | 12/2016 | Mills | |
| D804,659 S | 12/2017 | Hood | |
| 2002/0165493 A1 * | 11/2002 | Bierman | A61M 25/02 604/174 |
| 2002/0165494 A1 * | 11/2002 | Bierman | A61M 25/02 604/174 |
| 2007/0038182 A1 | 2/2007 | Bialecki | |
| 2007/0066958 A1 | 3/2007 | Wright | |
| 2009/0182283 A1 | 7/2009 | Sloan | |
| 2010/0179483 A1 | 7/2010 | Wright | |
| 2011/0295210 A1 | 12/2011 | Wright | |
| 2014/0276440 A1 * | 9/2014 | Wallace | A61M 25/02 604/180 |
| 2015/0038912 A1 | 2/2015 | Karim | |
| 2015/0133891 A1 * | 5/2015 | Rosenhan | A61M 25/02 604/509 |

OTHER PUBLICATIONS

C.R. Bard, Inc., Bard Medical, StatLock Foley Stabilization Device Brochure (2010); pp. 1-2.
European Search Report for European Patent Application No. 17877505.2 dated Jul. 10, 2020.

* cited by examiner

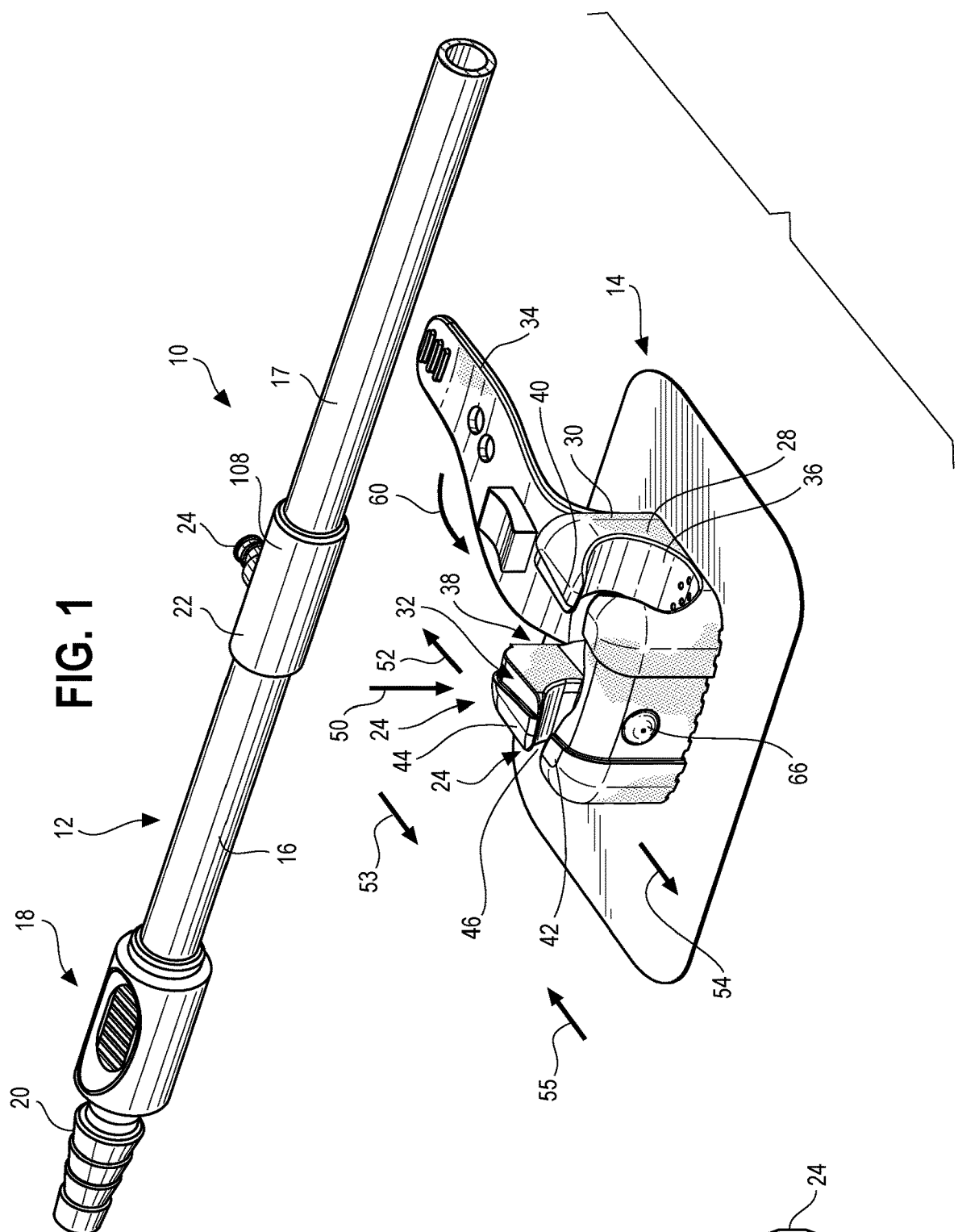
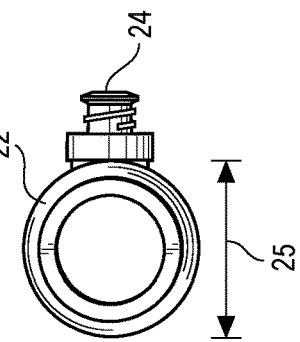

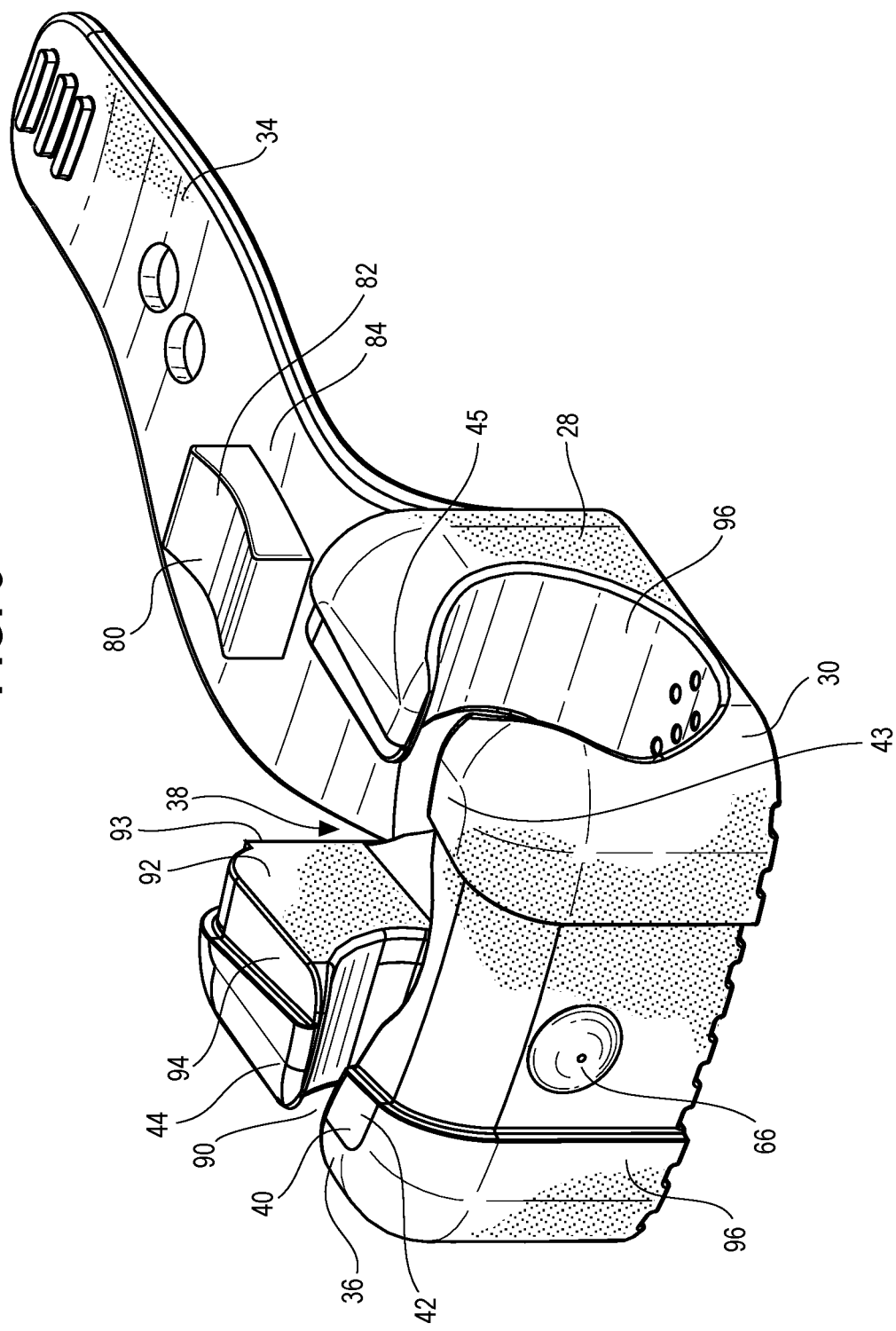

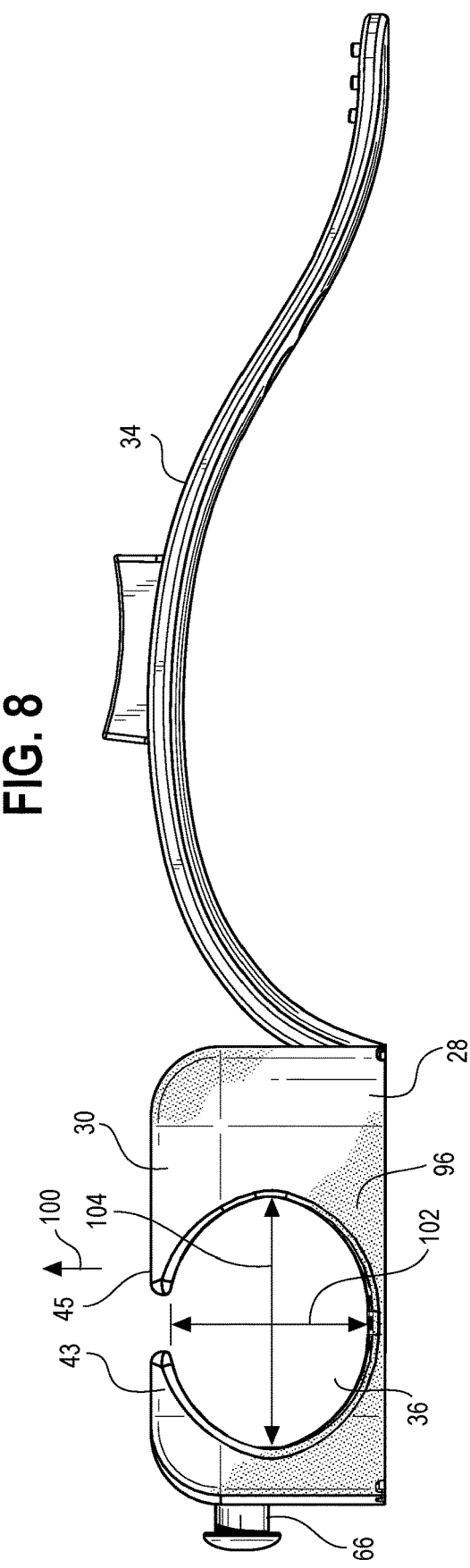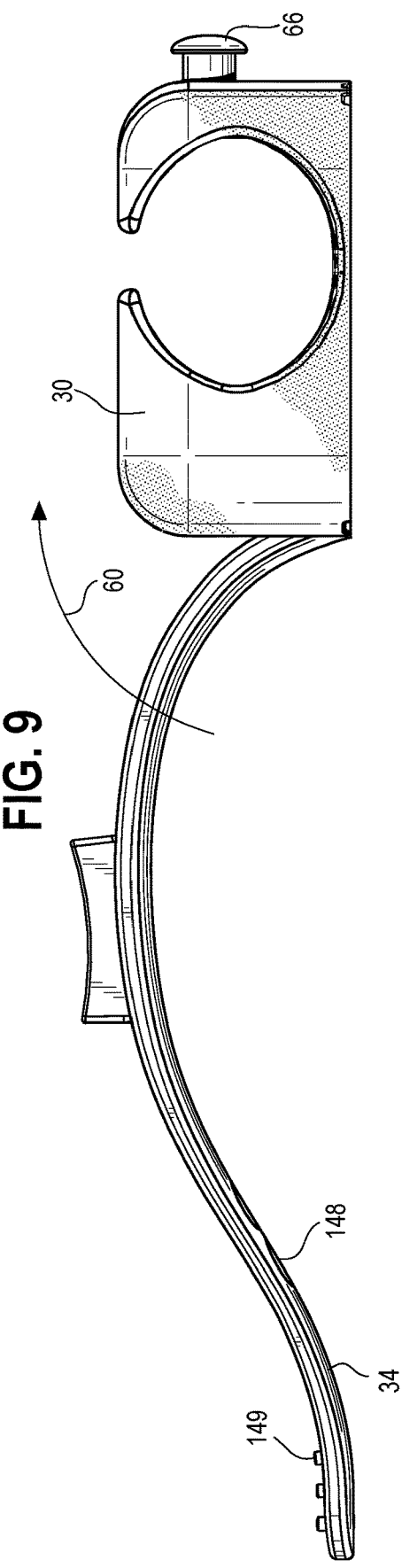

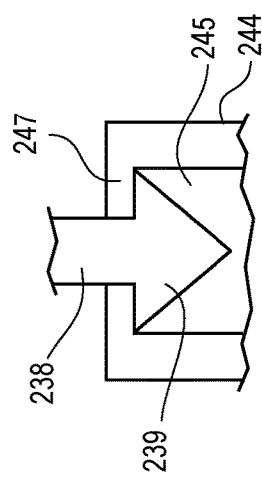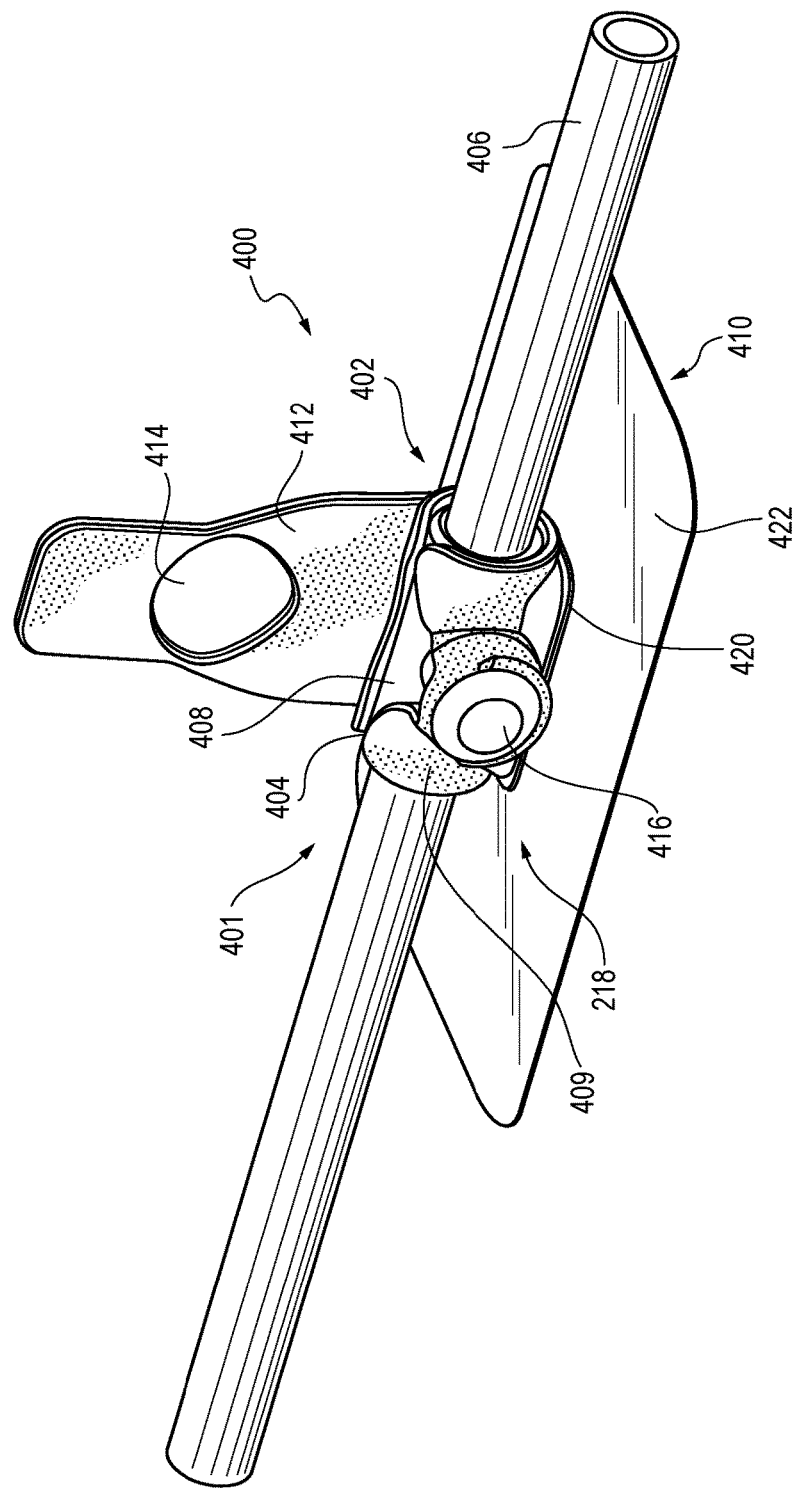

SECUREMENT DEVICE AND ASSEMBLY

RELATED APPLICATION

This application claims the benefit of U.S. Provisional Application No. 62/430,182 filed on Dec. 5, 2016, which is incorporated herein by reference in its entirety.

TECHNICAL FIELD

This disclosure relates to catheterization systems and, more specifically, to securement devices of catheterization systems for securing a component of a catheterization system relative to a patient.

BACKGROUND

Securement devices are used in catheterization systems to secure tubing of the catheterization system relative to the patient. The tubing may include a port for connecting a syringe and withdrawing fluid from within the tubing. The securement device may include an adhesive pad that is applied to the skin of a patient. It is known that catheterization tubing can cause chafing and a range of symptoms ranging from minor discomfort to pressure ulcers. It is therefore generally desired to provide a securement device that inhibits these symptoms.

BRIEF DESCRIPTION OF THE DRAWINGS

FIG. 1 is a perspective view of a catheter securement system including a catheter tube assembly and a securement device assembly;

FIG. 2 is an axially oriented front elevational view of a luer port connector of the catheter tube assembly of the system shown in FIG. 1.

FIG. 3 is a perspective view of a securement device of the securement device assembly shown in FIG. 1 shown with a strap of the securement device in a fully opened position.

FIG. 8 is a first side elevational view of the securement device shown in FIG. 3.

FIG. 9 is a second side elevational view of the securement device shown in FIG. 3.

FIG. 20 is a schematic view of an alternative embodiment of an interface between upper and lower members of a pivot member of the securement device assembly of FIG. 18.

FIG. 21 is a perspective view of a catheter securement system including a catheter tube assembly and a securement device assembly.

DETAILED DESCRIPTION

Figure 4:
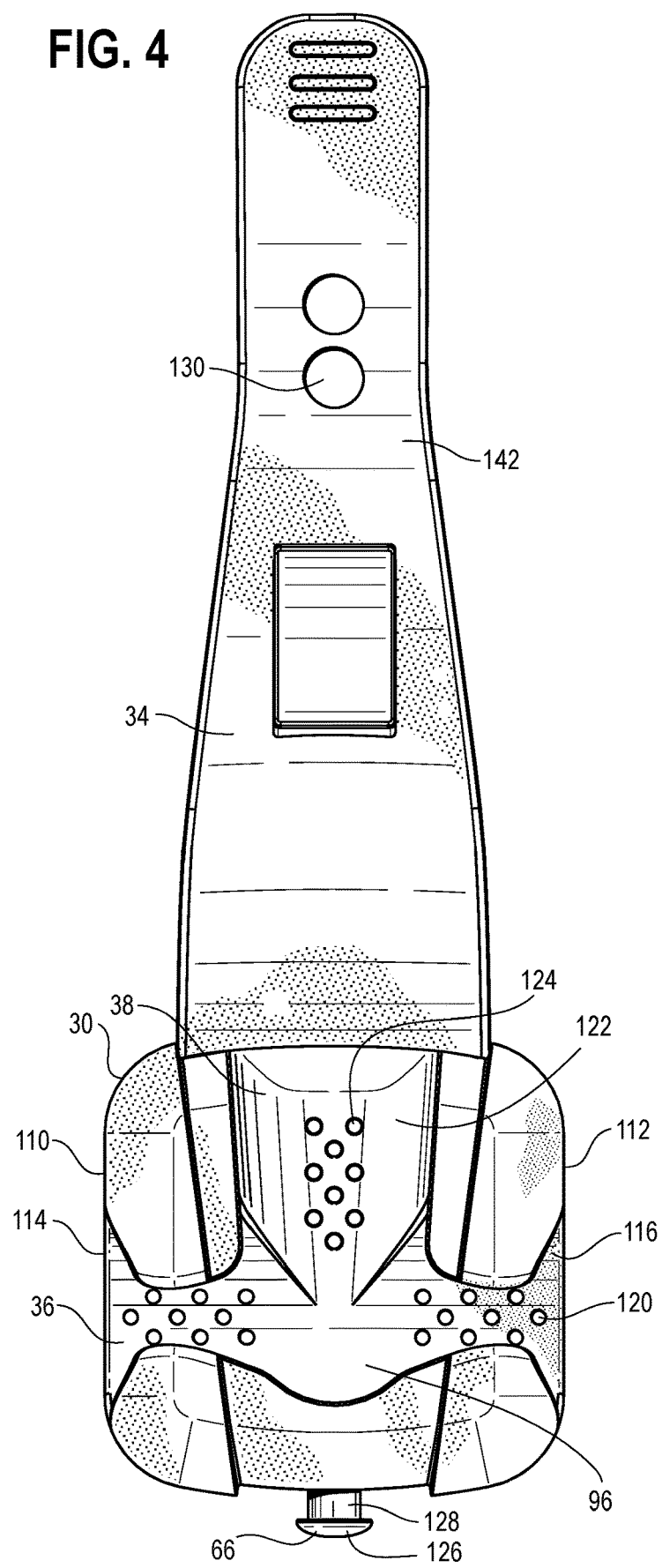
FIG. 4 is a top plan view of the securement device shown in FIG. 3.

Generally, it has now been found that a catheterization system that includes a securement device with a body portion and a strap portion. Generally, the body portion includes an upper surface and a lower surface and a pocket that comprises a substantially tubular channel, the channel being open at the upper surface, the pocket further including a port cavity in communication with the channel. The securement device further comprises a strap portion movable between a fully closed position and a range of open positions. The strap portion at least partially covers pocket when in a closed position thereby closing the channel at the upper surface but allows access to the channel when in an open position.

With reference to FIG. 1, a catheter securement system 10 is provided that includes a catheter tube assembly 12 that may be releasably connected to a securement device assembly 14. The catheter tube assembly 12 includes tubes 16, 17, a barbed plug 20 for connecting to other tubing, and tube structures such as a vent 18 and a port fitting 22. The port fitting 22 includes a port 24, preferably a luer port, which permits a syringe to be connected to the catheter tube assembly 12 and withdraw fluid such as urine from within the catheter tube assembly 12. The securement device assembly 14 includes a securement device 28 having a body portion 30 with a pocket 32 for receiving a portion of the catheter tube assembly 12 such as the port fitting 22 or the vent 18. The securement device 28 further includes a strap portion 34 for closing the pocket 32 and retaining the tube structure therein. The body portion 30 and the strap portion 34 may have a monolithic construction, or may comprise two components joined together. The strap portion 34 has one or more open positions that permit the catheter tube assembly 12 to be advanced into and out of the pocket 32 and one or more closed positions where the strap portion 34 secures the portion of the tube assembly 12 in the pocket 32.

The pocket 32 of the body portion 30 includes a channel 36 extending across the body portion 30 and a cavity 38 extending transversely away from the channel 36. The channel 36 and the cavity 38 form a generally T-shaped cavity in the body portion 30. The channel 36 may be tubular in shape and may be oblong. The term oblong is intended to refer to a shape that is wider than it is tall. With reference to FIG. 8, the channel 36 may have a width 104 that is greater than a height 102 as one example. With reference to FIG. 2, the port fitting 22 may have a dimension 25 thereacross that is less than the width 104 of the pocket 36 to permit toggling of the catheter tube assembly 12 as discussed below.

The body portion 30 includes an upper surface 40 and the channel 36 and the cavity 38 open to the upper surface 40. The channel 36 includes pairs of spaced portions 42, 44 and 43, 45 each separated by a gap 46. The channel 36 permits the port fitting 22 or other portion of the port fitting 22 to be advanced downward in direction 50 against the portions 42, 44 and 43, 45 to thereby engage the portions 42, 44 and 43, 45 such that they shift apart in directions 52, 54 to thereby permit the port fitting to be inserted into the channel 36.

The body portion 30 may be made of a resilient material, such as silicone having a Shore A hardness durometer rating in the range of 40-80, preferably a Shore A hardness of about 60. Such material permits the portions 42, 44 and 43, 45 to be sufficiently pliable to deflect apart and out of the way of the catheter tube assembly 12 but sufficiently durable to retain the assembly 12. In one approach, the body portion 30 and strap portion 34 are monolithically formed by injection molding a silicone material.

When the port fitting 22 engages and separates the portions 42, 44 and 43, 45 of the channel 36, the channel 36 is thereby reconfigured to a pass-through configuration whereby the port fitting 22 may be advanced into and seated in the channel 36. In one approach, the port 24 is aligned with the cavity 38 so that as the port fitting 22 is advanced in direction 50 into the channel 36, the port 24 is advanced into the cavity 38. Once the port fitting 22 and port 24 have been positioned in the channel 36 and the cavity 38, the resilient properties of the body portion 30 urge the portions 42, 44 and 43, 45 back together in directions 53, 55 above the port fitting 22. In this manner, the channel 36 returns to a retention configuration thereof such that the portions 42, 44 and 43, 45 retain the port fitting 22 in the channel 36. To secure the catheter tube assembly 12 in the channel 36, the strap portion 34 is then pivoted in direction 60 to a closed position and secured using a plug 66 so that the strap portion 34 is held in the closed position and maintains the port fitting 22 in the channel 36 and cavity 38. As shown, the plug 66 is a separately molded part, preferably of the same material as the body portion, and the plug 66 may be monolithic with the body portion in other embodiments.

With reference to FIG. 2, the port 24 may be a luer port. The luer port 24 allows a needless syringe to be connected to the catheter tube assembly 12. The ability to connect the syringe without using a needle improves the ease of withdrawing fluid from within the catheter tube assembly 12.

Figure 12:
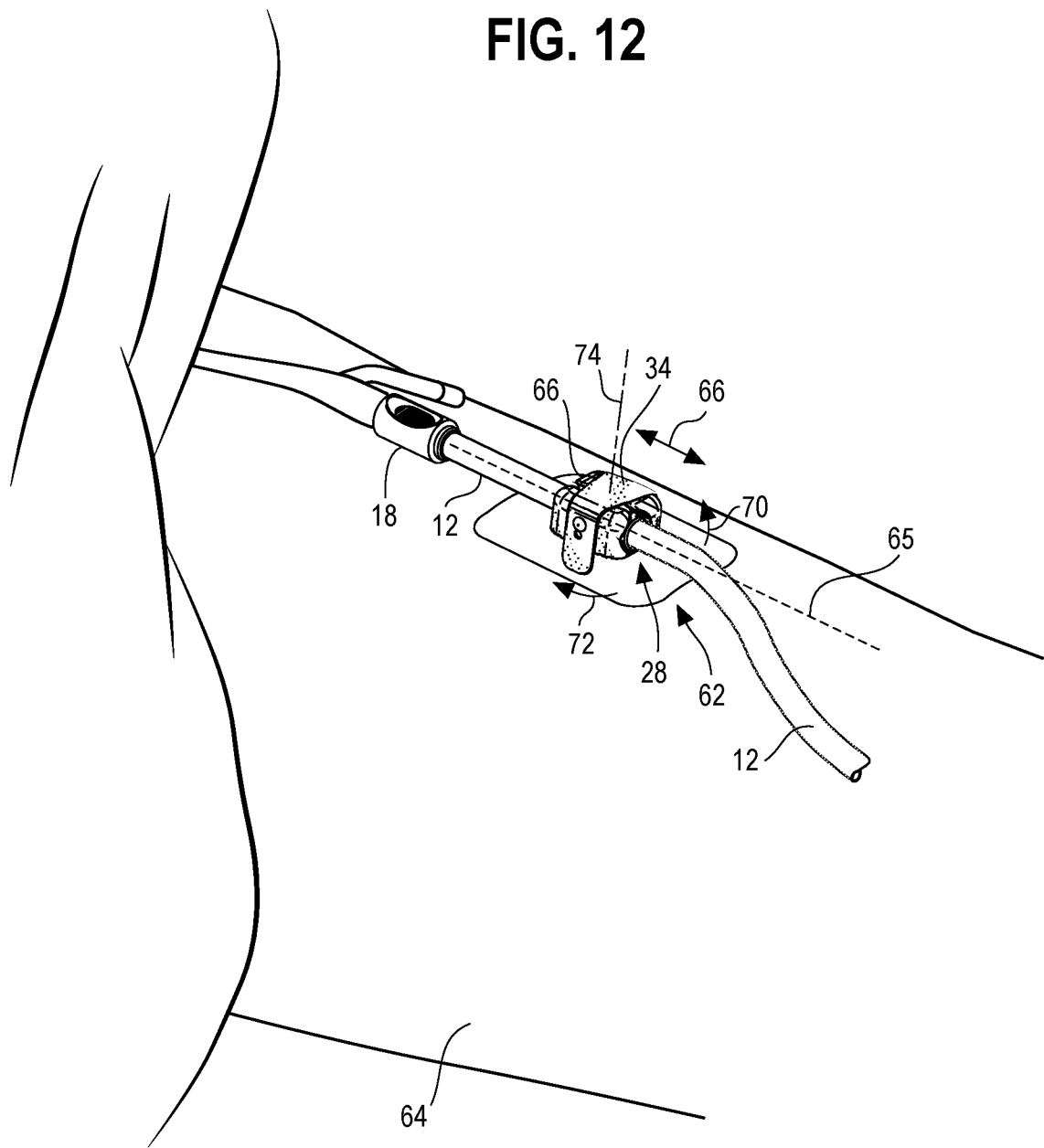
FIG. 12 is a perspective view of the catheter securement system shown in FIG. 1 disposed on the leg of a patient, showing the strap in the closed position and retaining a luer port fitting of the catheter tube assembly in the securement device.

Turning to FIG. 12, the securement device assembly 14 includes a support structure 62 for securing the securement device 14 to the skin of a patient, such as a leg 64. The port fitting 22 is shown positioned in the channel 36 of the securement device 28 and the strap portion 34 has been pivoted to a closed position thereof to cover the channel 36. The plug 66 holds the strap portion 34 in the closed position, as discussed in greater detail below. With the strap portion 34 in the closed position thereof, the securement device assembly 14 resists axial movement of the catheter tube assembly 12 along a longitudinal axis 65 in directions 66. The securement device assembly 14 permits pivoting of the catheter tube assembly 12 in directions 70, 72 throughout a predetermined angle 190 (see FIG. 14) about an axis 74 extending perpendicular to the axis 65, such as 30-40 degrees. In this manner the securement device will accommodate patient movement and jostling of the device.

Returning to FIG. 3, the securement device 28 is shown including the strap portion 34 in an open position thereof. The strap portion 34 has a protrusion, such as a pad 80, with a curved surface 82 for contacting a portion of the catheter tube assembly 12, such as the port fitting 22. The pad 80 is raised from a surface 84 of the strap portion 34 such that the pad 80 extends into the pocket 32. Because the pad 80 extends into the pocket 32, the pad 80 engages and pinches the port fitting 22 between the pad 80 and a curved lower portion 96 (see FIG. 4) of the body portion 30. In one approach, the parts are sized relative to one another such that the pinch very slightly deforms the port fitting 22 to thereby restrict axial movement of the catheter tube assembly 12.

The channel 36 includes an opening 90 at the upper surface 40 of the body portion 30 through which the port fitting 22 is advanced into the channel 36. The cavity 38 also includes an opening 92 at the upper surface 40 that may be contiguous with the opening 90. In this manner, the port fitting 22 may be advanced into the channel 36 through the opening 90 and the port 24 may be advanced into the cavity 38 through the opening 92. The cavity 38 may open to a rear surface 93 of the body portion 30. In another embodiment, the body portion 30 may include a wall (not shown) separating the cavity 38 from the rear surface 93.

The body portion 30 includes a recessed area 94 extending along the upper surface 40 and a front surface 96 and is configured to receive the strap portion 34. In this manner, when the strap portion 34 is in a closed position thereof, the strap portion 34 may be flush with the upper surface 40 and the front surface 96 of the body portion 30. This reduces the risk of the strap 34 catching on an object and disengaging form the plug 66.

With reference to FIGS. 3 and 8, the curved lower portion 96 is disposed below the portions 43, 45. The curved lower portion 96 supports the underside of the port fitting 22 while the portions 41, 43 extend over the port fitting 22 to resist the port fitting 22 from moving in direction 100 out of the channel 36. Due to the width 104 of the channel 36 being larger than the width 25 of the port fitting 22, the port fitting 22 may pivot in directions 70, 72 while a center portion 108 (see FIG. 1) of the port fitting 22 is pinched and held in place by the pad 80 and the curved lower portion 96.

Figure 5:
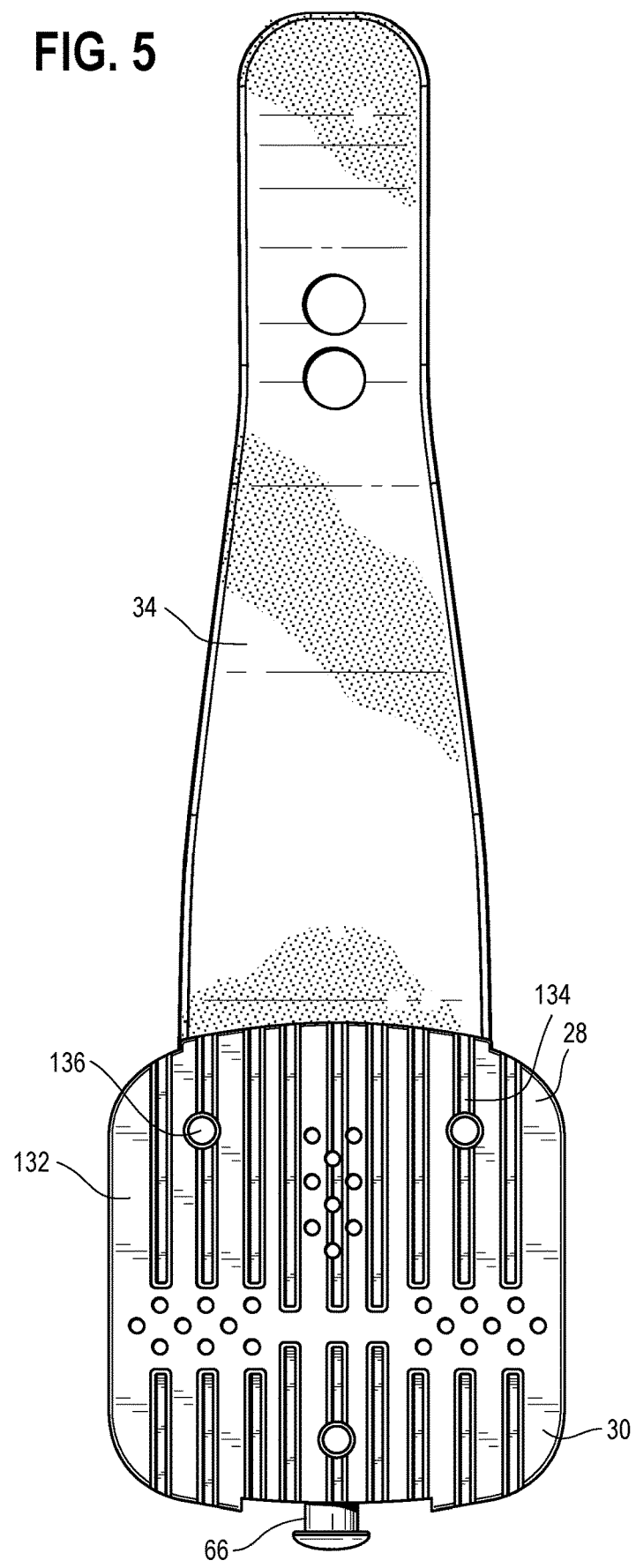
FIG. 5 is a bottom plan view of the securement device shown in FIG. 3.

Turning to FIG. 4, the body portion 30 includes opposite sides 110, 112 and the channel 36 includes generally elliptical openings 114, 116 that open to the sides 110, 112. The curved lower portion 96 of the channel 36 includes through openings 120 to permit air to flow beneath the port fitting 22. Similarly, the cavity 38 includes a lower portion 122 having through openings 124 therein. The through openings 120, 124 improve the breathability of the securement device assembly 14. With reference to FIG. 5, the body portion 30 includes a lower surface 132 with ventilation grooves 134 therein. The grooves 134 permit airflow under the body portion 30. The body portion 30 also includes one or more blind openings 136 that receive one or more posts 138 of a retainer 140 (see FIG. 11).

The plug 66 includes an enlarged end 126 and a shaft 128. The strap portion 34 includes one or more openings 130 that are sized to receive the plug 66. A plurality of openings 130 may be used to provide a user the ability to position the strap portion 34 at one of a plurality of closed positions that best corresponds to the portion of the catheter tube assembly 12 received in the pocket 32. For example, one of the openings 130 may be used for a smaller diameter port fitting 22 and another one of the openings 130 may be used for a larger diameter port fitting 22.

When connecting the strap portion 34 to the plug 66, the enlarged end 126 may deform the material around the opening 130 as the strap portion 34 is fit onto the plug 66. Once the shaft 128 extends through the opening 130, the material around the opening 130 may relax due to the shaft 128 having a smaller maximum diameter than the maximum diameter of the enlarged end 126. Further, the enlarged end 126 resists the strap portion 34 disengaging from the plug 66.

Figure 6:
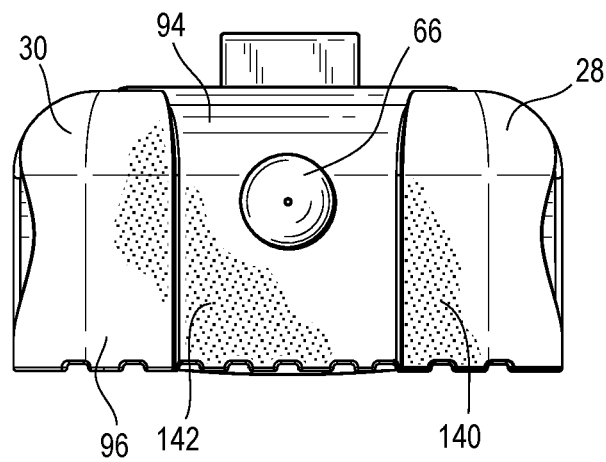
FIG. 6 is a front elevational view of the securement device shown in FIG. 3.
Figure 7:
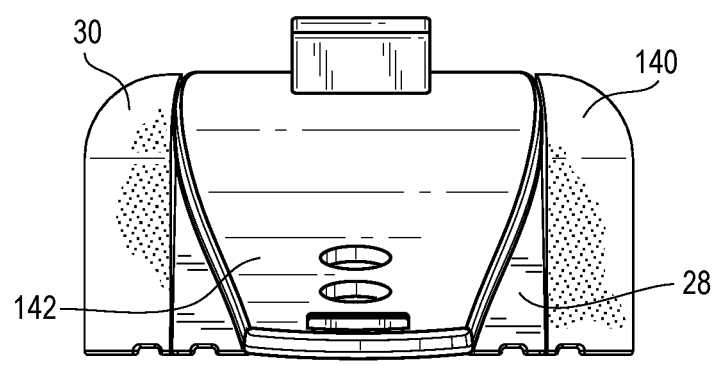
FIG. 7 is a rear elevational view of the securement device shown in FIG. 3.
Figure 11:
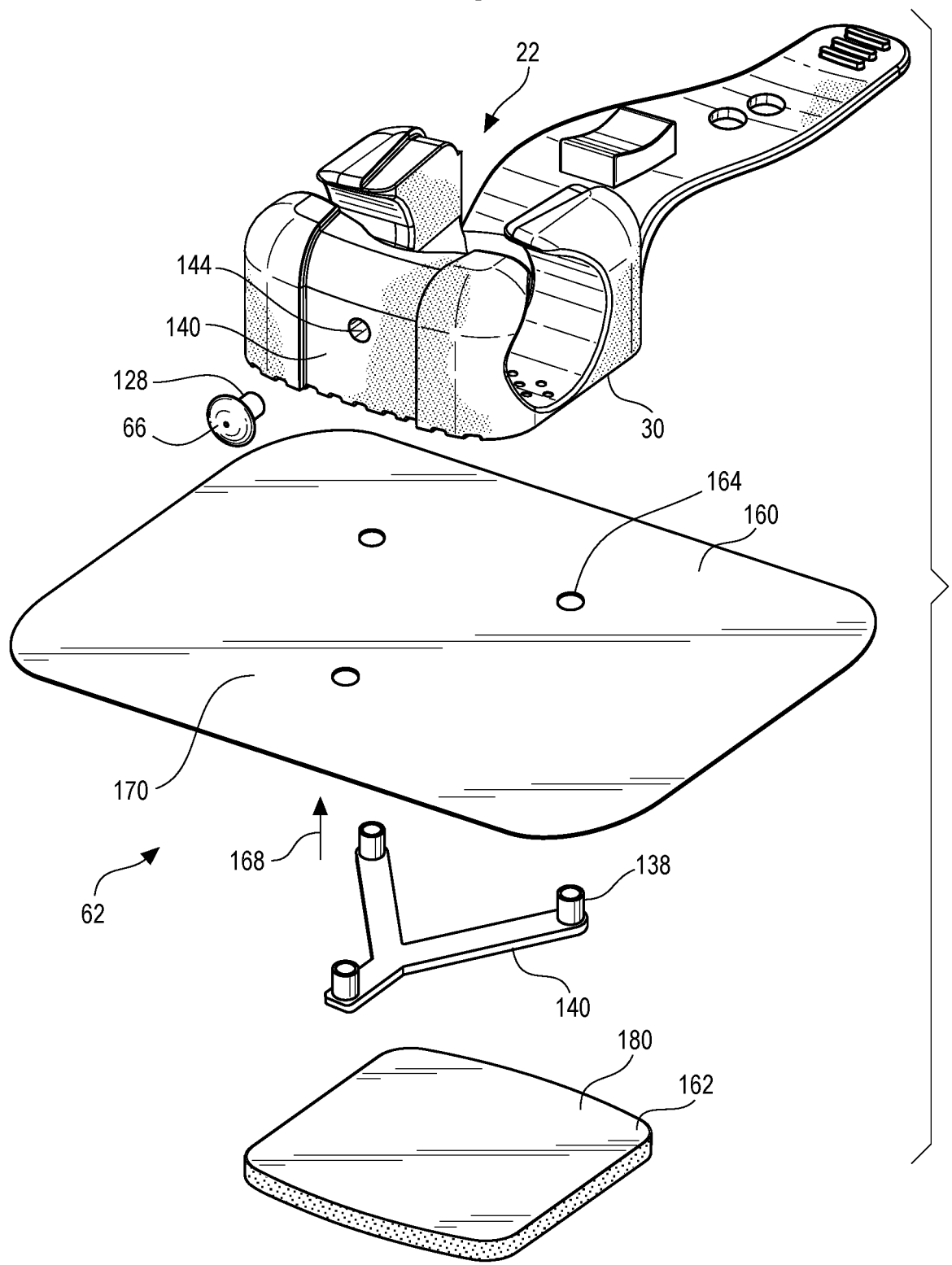
FIG. 11 is an exploded view of the securement device assembly of the catheter securement system shown in FIG. 1.

With reference to FIGS. 6 and 7, the body portion 30 includes a front wall 140 that includes a portion 142 of the recessed area 94. The recessed area portion 142 receives a distal portion 148 of the strap portion 140 so that the distal portion 148 is flush with the front surface 96 of the body portion 30. With reference to FIG. 11, the front wall 140 also includes an opening 144 that receives the plug 66. In one approach, the shaft 128 of the plug 66 is press fit into the opening 144 of the front wall 140.

With reference to FIG. 9, the strap portion 34 may be generally pivoted in direction 60 throughout a range of open positions until the distal portion 148 is positioned to receive the plug 66 in the one or more openings 130. The distal portion 134 includes nubs 149 to make it easier for a user to grasp the distal portion 134. Once the plug 66 is received in one of the openings 130 to secure the strap portion 34 in the respective closed position, the engagement of the plug 66 and the strap portion 34 resists movement of the strap portion 34 away from the closed position thereof. The distal portion 148 of the strap portion 34 may extend to or beyond the lower surface 132 of the body portion 30 when the strap portion 34 is in the closed position thereof.

Figure 10:
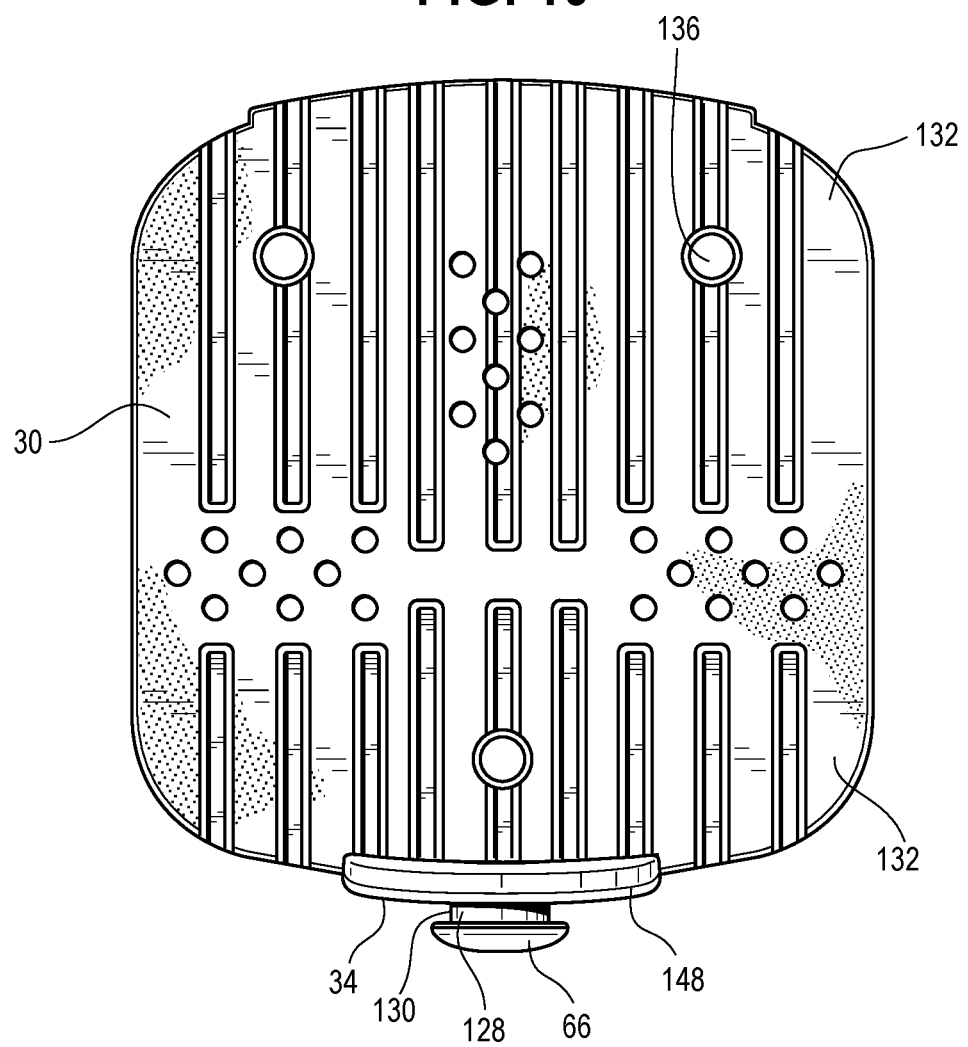
FIG. 10 is a bottom plan view of the securement device shown in FIG. 3 showing the strap in a fully closed position.

With reference to FIG. 11, the support structure 62 includes a support material 160, such as a non-woven acrylic material. The support structure 62 may also include the retainer 140 and a foam underpad 162. The support material 160 has openings 164 arranged in a pattern that corresponds to the pattern of the posts 138 of the retainer 140. In this manner, the posts 138 may be advanced in direction 168 through the openings 164 and into the blind openings 136 (see FIG. 10) of the lower surface 132 of the body portion 30. This captures the support material 160 between the body portion 30 and the retainer 140. In one approach, an adhesive may be used to secure the posts 138 within the blind openings 136 of the body portion 30 to secure the support material 160 between the body portion 30 and the retainer 140. Further, an adhesive may be used to secure an upper surface 170 of the support material 160 to the lower surface 132 of the body portion 30. The combination of the retainer 140 engaged with the body portion 30 and the adhesive securing the support material 160 to the body portion 30 creates a durable construct for connecting the body portion 30 to the patient via the support material 160.

Figure 15:
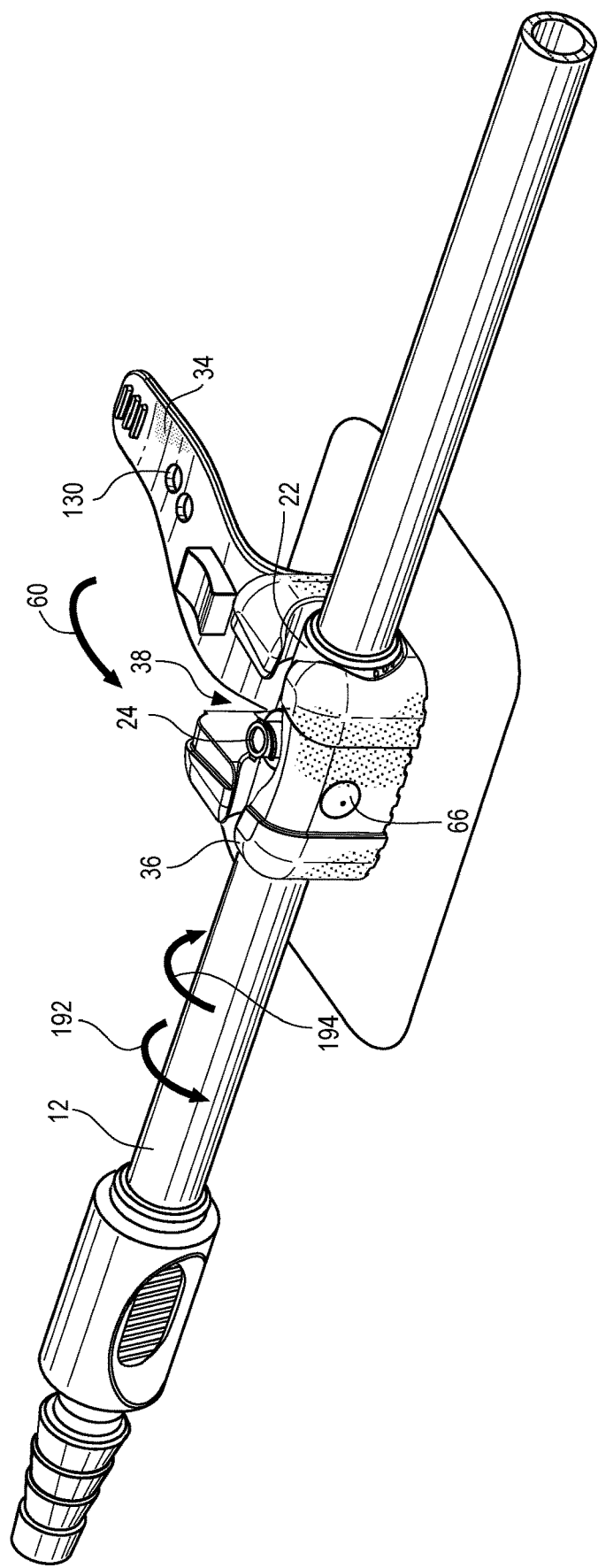
FIG. 15 is a perspective view of the catheter securement system shown in FIG. 13 illustrating the luer port rotated out of the luer port cavity and into an access position.
Figure 16:
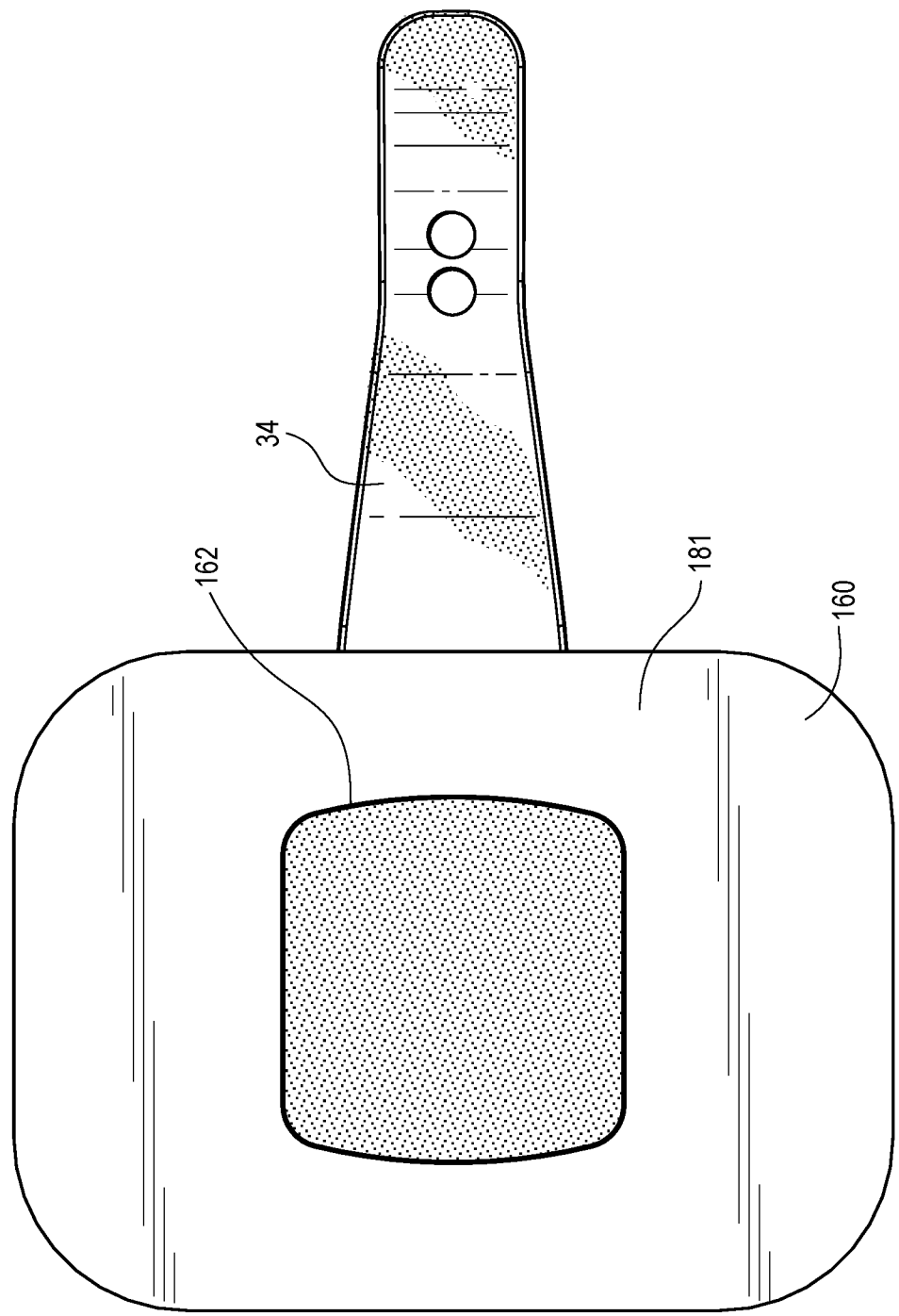
FIG. 16 is a bottom plan view of the securement device assembly of the catheter securement system shown in FIG. 1.

To secure the foam underpad 162 to the support material 160, an adhesive may be used to secure an upper surface 180 of the foam underpad 162 to a lower surface 181 of the support material 160 (see FIG. 16). With reference to FIGS. 15 and 16, the upper surface 170 of the support material 160 preferably has a larger surface area than the lower surface 132 of the body portion 30 and likewise preferably has a larger surface area than upper surface 180 of the foam underpad 162. Polyurethane adhesive may be used on the underside of the support material 160 and optionally the underside of the foam underpad 162.

Figure 13:
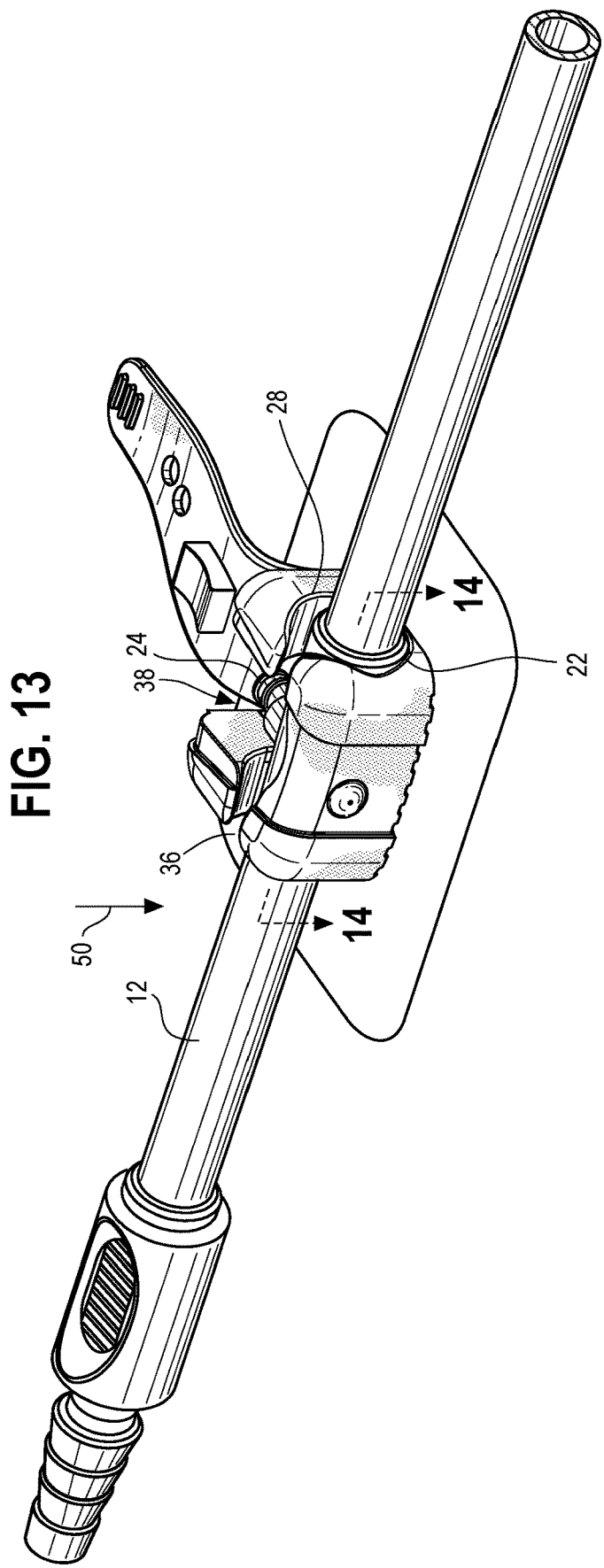
FIG. 13 is a perspective view of the catheter securement system shown in FIG. 1 showing the strap in a fully open position and showing the luer port in a secured position in a luer port cavity of the securement device.
Figure 14:
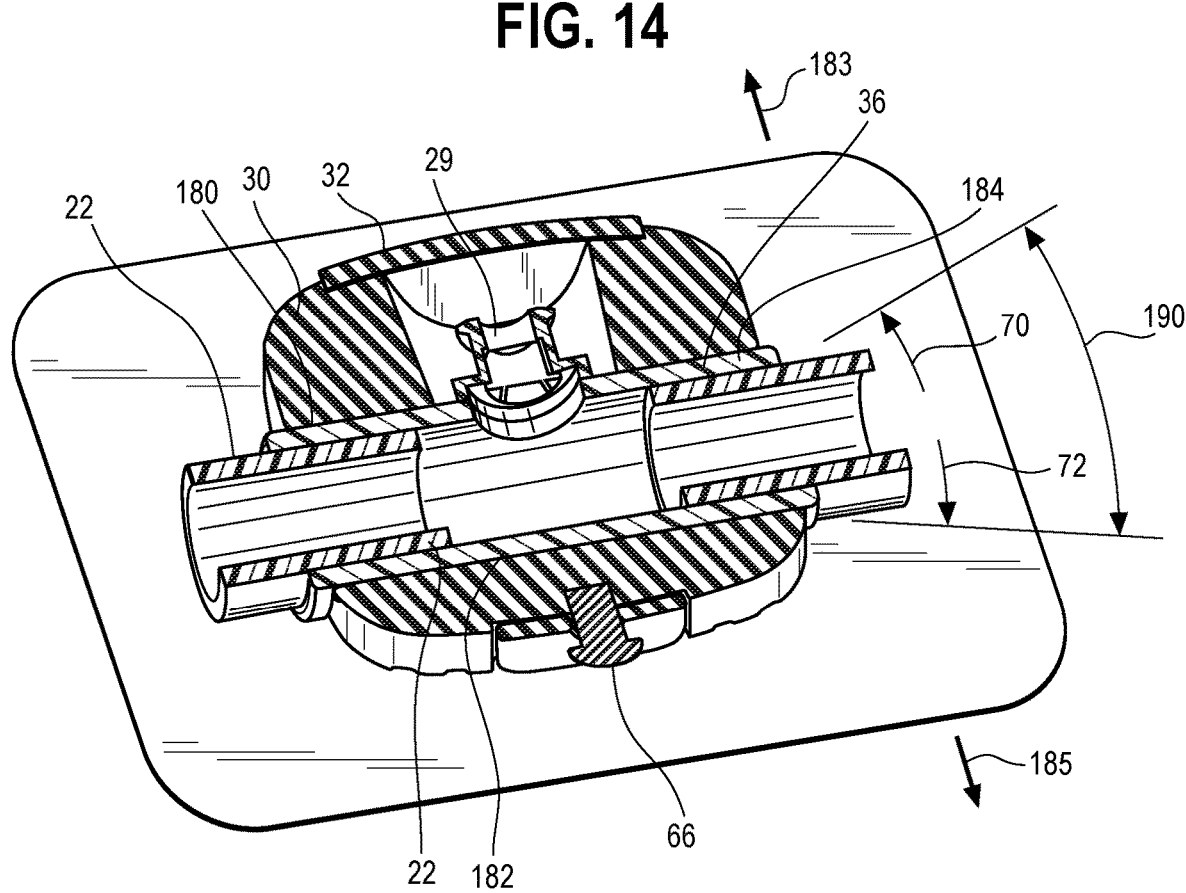
FIG. 14 is a cross sectional view taken along line 14-14 in FIG. 13.

With reference to FIG. 13, the port fitting 22 has been advanced in direction 50 causing the portions 42, 44, and 43, 45 to shift apart in directions 52, 54 which allows the port fitting 22 to be advanced into the channel 36. Likewise, the port 24 has advanced into the cavity 38. Turning to FIG. 14, the channel 36 includes wall portions 180, 182, 184 configured to contact the port fitting 22 and limit movement of the port fitting 22 in directions 183, 185. Further, with the center portion 108 of the port fitting 22 pinched by the pad 80 and held in place within the channel 36, the wall portions 180, 182, 184 contact and limit pivoting of the port fitting 22 to a predetermined range of movement, such as an angle 190 of 30-40 degrees. As noted above, the channel 36 has a wider width 104 (see FIG. 8) which permits this toggling of the port fitting 22 in the channel 36.

With reference to FIG. 15, the catheter tube assembly 12 can be turned in direction 192 to rotate the port 24 out of the cavity 38 and into an access orientation. The port 24 may now be readily accessed by a syringe to withdraw fluid from within the catheter tube assembly 12. Once the fluid has been withdrawn, the user may turn the catheter tube assembly 12 back in direction 194 to move the port 124 back into the cavity 138. The securement device 28 can be closed by pivoting the strap portion 34 in direction 60 back to a closed configuration and engaging one of the openings 130 with the plug 66 to thereby return the catheter tube assembly 12 to a secured position.

Figure 17:
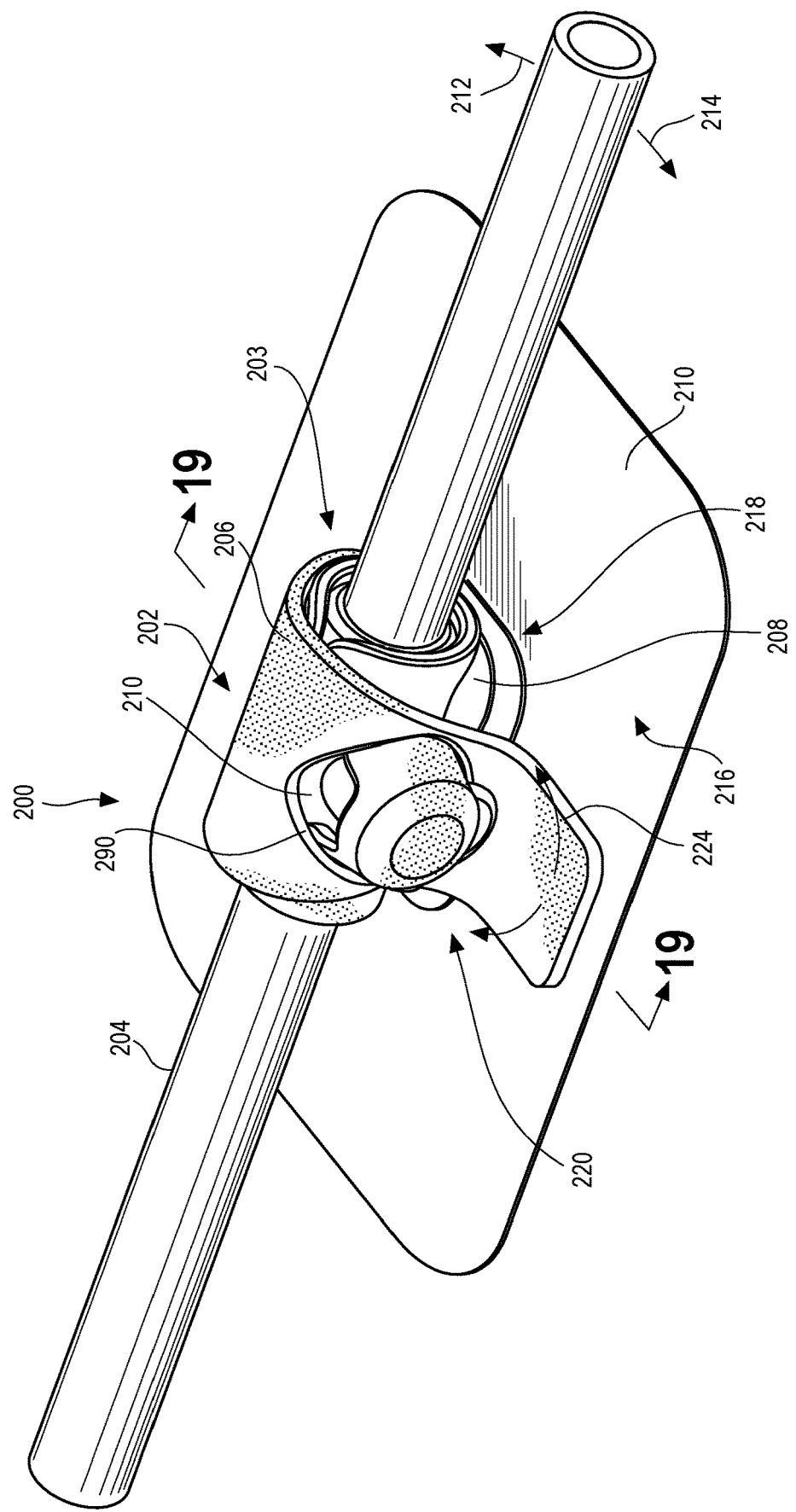
FIG. 17 is a perspective view of a catheter securement system showing a strap of a securement device assembly of the catheter securement system in a closed position and retaining a luer port fitting of a catheter tube assembly of the catheter securement system in the securement device assembly.
Figure 18:
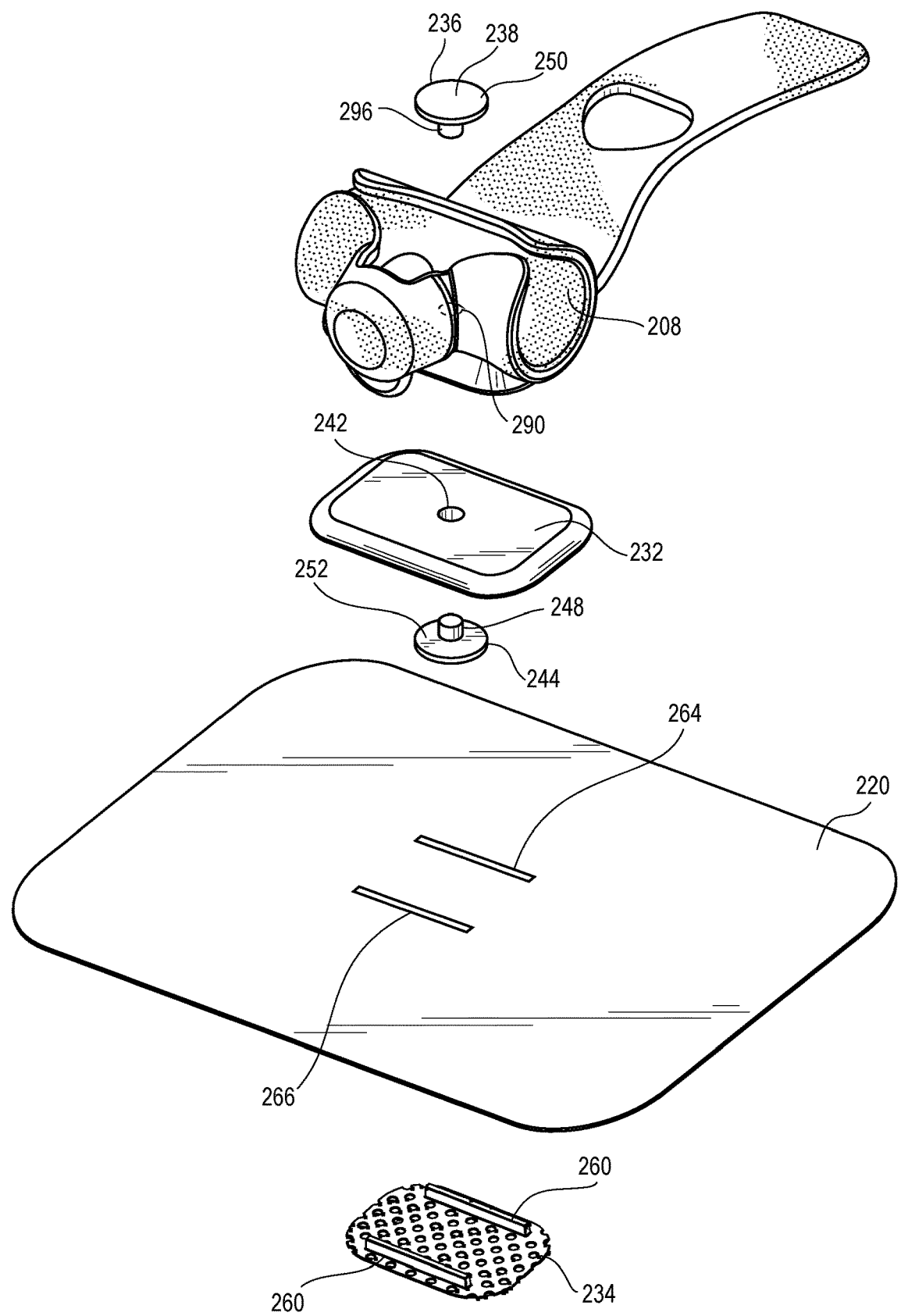
FIG. 18 is an exploded view of the securement device assembly shown in FIG. 17.
Figure 19:
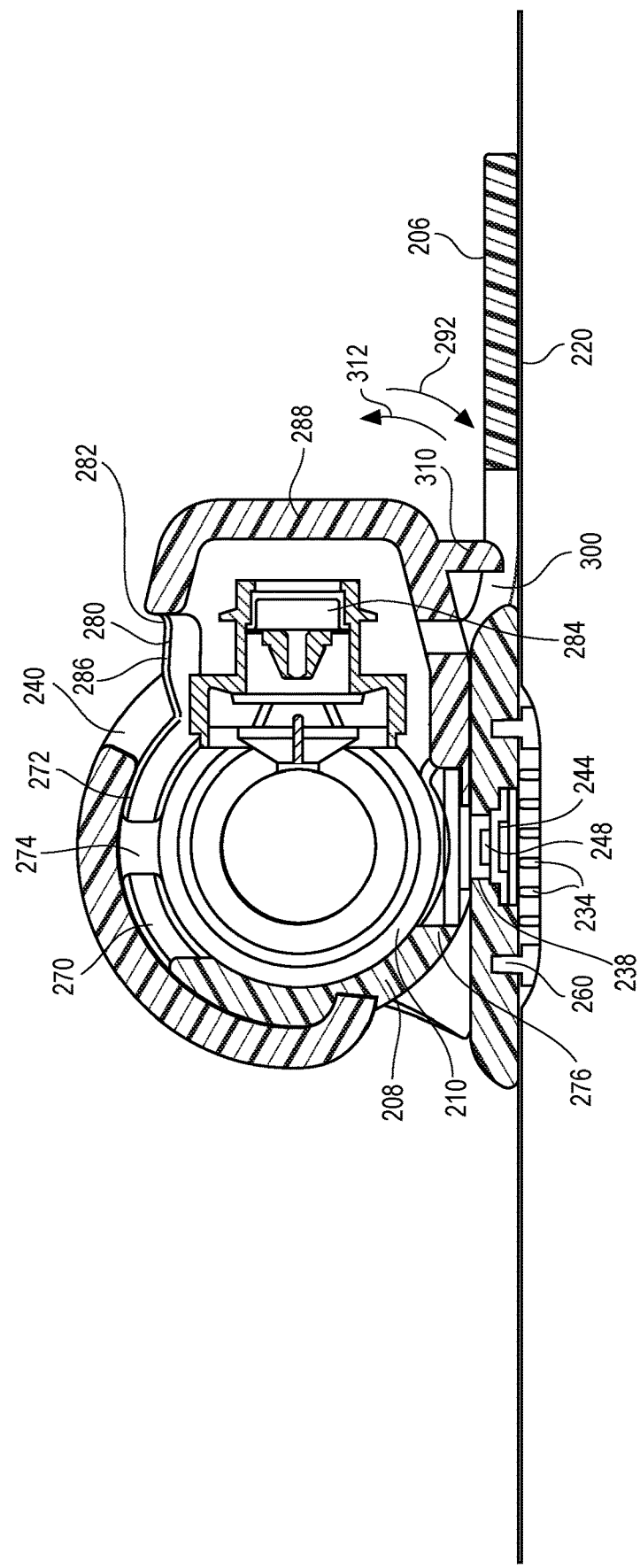
FIG. 19 is a cross sectional view taken along line 19-19 in FIG. 17.

With reference to FIGS. 17-19, the catheter securement system 200 includes a securement device assembly 202 that releasably secures a catheter tube assembly 204 as shown in FIG. 17. The securement device assembly 202 includes a securement device 203 having a strap portion 206 and a body portion 208. The strap portion 206 holds a port fitting 210 of the catheter tube assembly 204 in a pocket 209 (see FIG. 18) of the body portion 208 while permitting the catheter tube assembly 204 to pivot in directions 212, 214. The pocket 209 includes a substantially tubular channel 211 and a port cavity 282 in communication therewith. The securement device assembly 202 includes a support structure 216 having a support material 220 for contacting the skin of a patient and a pivot connection 218 pivotally connecting the support structure 216 to the securement device 203. The pivot connection 218 allows the securement device 203 and the catheter tube assembly 204 retained therein to turn in directions 222, 224 relative to the support material 220. In this manner, the securement device assembly 202 accommodates movement of the catheter tube assembly 204 such as due to patient movement.

With reference to FIGS. 17 and 18, the support structure 216 includes a retainer 230 having an upper portion 232 and a lower portion 234. The support structure 216 further includes a pivot member 236 that pivotally connects the retainer 230 to the body portion 208. In one form, the pivot member 236 includes an upper member 238 and a lower member 238 that are joined together during assembly of the securement device assembly 204. The pivot member 236 extends through an opening 240 (see FIG. 19) in the body portion 208 and through an opening 242 of the retainer upper portion 232. The upper and lower members 238, 244 include disk portions 250, 252 that are positioned on opposite sides of the body portion 208 and the retainer upper portion 232 to hold together the body portion 208 and the retainer upper portion 232. In one approach, the upper member 238 has a socket 246 that receives a projection 248 of the lower member 244, such as with snap-fit engagement. As another example, with reference to FIG. 20, the upper member 238 may have a barb 239 and the lower member 244 may have a socket 245 with a collar 247. When the upper and lower members 238, 244 are assembled, the the barb 239 is snapped past the collar 247. The collar 247 retains the barb 239 within the socket 245 while permitting the upper member 238 to turn relative to the lower member 244.

With reference to FIGS. 18 and 19, the retainer lower portion 234 includes projections 260 that extend through openings 264, 266 of the support material 220 and into corresponding sockets 262 of the retainer upper portion 232. The projections 260 may be secured in the sockets 262 using adhesive which secures the retainer upper and lower portions 232, 234 together. In this manner, the retainer upper portion 232 and the lower portion 234 are secured together with the support material 220 sandwiched therebetween.

As shown in FIG. 19, the body portion 208 includes a pair of spaced portions 270, 272 separated by a gap 274 that separate as the catheter tube assembly 204 is pressed into the pocket 209 of the body portion 208 and return toward each other as the catheter tube assembly 204 is seated against a lower portion 276 of the pocket 209 to retain the catheter tube assembly 204 in the pocket 209. The strap portion 206 may then be pivoted to a closed position and connected to a plug 280 of the body portion 208. The strap portion 206 has an opening 290 that is fit over the plug 280 to hold the strap portion 206 in the closed position thereof. The plug 280 includes a shaft 286 and an enlarged end 288 for holding the strap portion 206 in the closed position. The plug 280 may also define at least a portion of the cavity 282 for receiving a port 284 of the port fitting 210.

The strap portion 206 includes a portion 300 defining the opening 290 that may contact the shaft 286 of the plug 280 and firmly hold the strap portion 206 in the closed position thereof. Further, the enlarged head 288 may contact the portion 300 and resist release of the strap portion 206 from the plug 280. The plug 280 may also include a lip 310 that provides additional resistance to movement of the strap portion 206 in direction 312.

With reference to FIG. 21, a catheter securement system 400 is provided that is similar in many respects to the catheter securement system 200 discussed above. The catheter securement system 400 includes a securement device assembly 401 having a securement device 402 with a body portion 409. The body portion 409 includes a generally tubular channel 404 for receiving a catheter tubing assembly 406 including a port fitting 408 thereof. The securement device assembly 401 includes a support structure 410 and a pivot connection 218 pivotally connecting the securement device 402 to the support structure 410. The securement device 402 includes a strap portion 412 with an opening 414 for being fit over a plug 416 of the securement device 402 and retaining the port fitting 408 within the channel 404. The support structure 410 includes a retainer 420 and a support material 422. The support material 422 may comprise an adhesive pad for being secured to the skin of a patient and the body portion 409 and the retainer 420 may be made of silicone.

Figure 22:
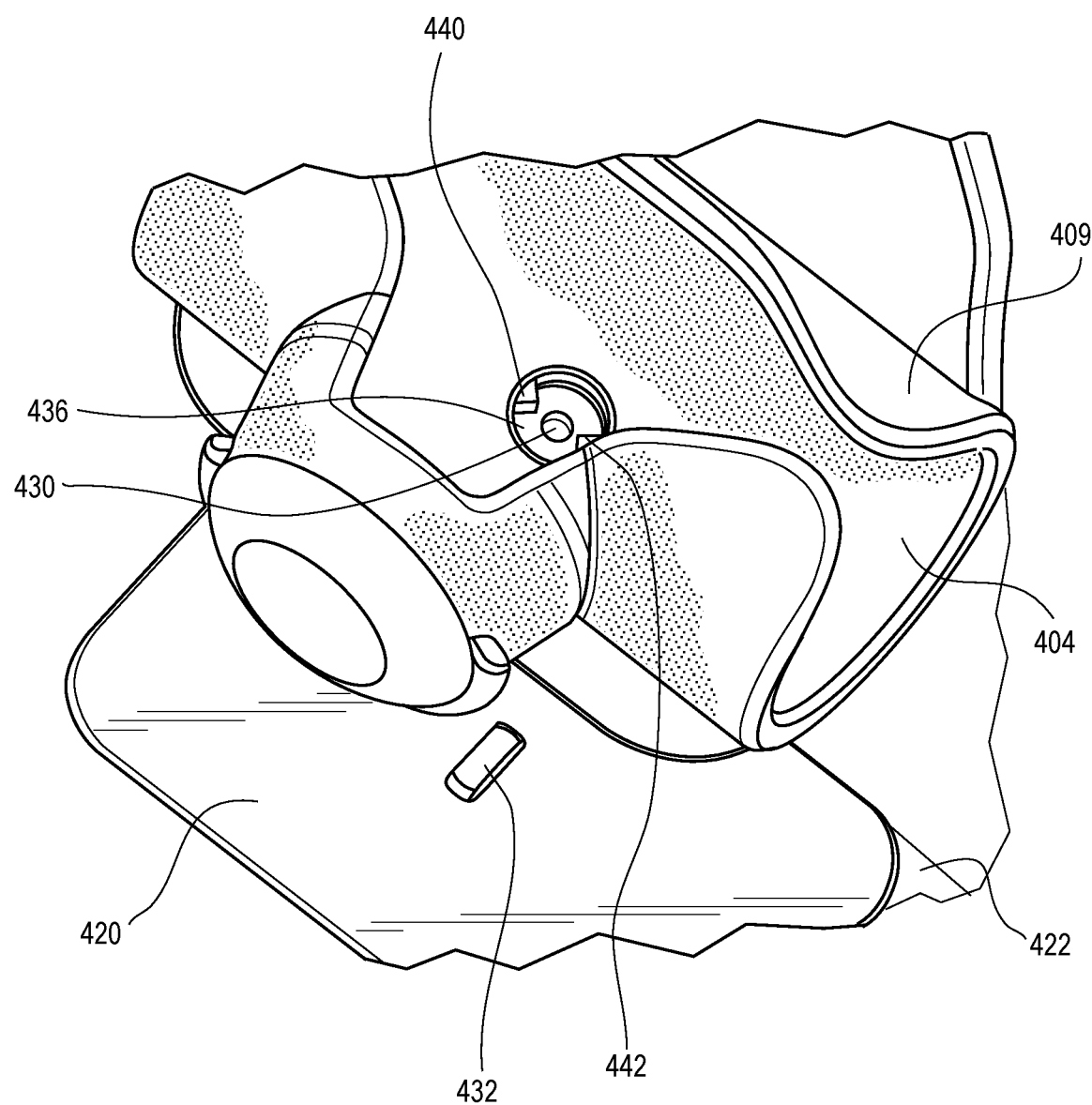
FIG. 22 is an exploded view of a portion of the catheter securement system of FIG. 21 showing an opening of a securement device of the securement device assembly that receives a pivot member of a retainer of the securement device assembly.

With reference to FIG. 22, the body portion 409 includes an opening 430 that receives a pivot member 432 of the retainer 420. The opening 430 has a countersunk portion 436 that receives an enlarged head 438 (see FIG. 23) of the pivot member 432. The body portion 409 includes a pair of stops 440, 442 on opposite sides of the opening 430 for limiting relative movement between the body portion 409 and the retainer 420, as discussed in greater detail below.

Figure 23:
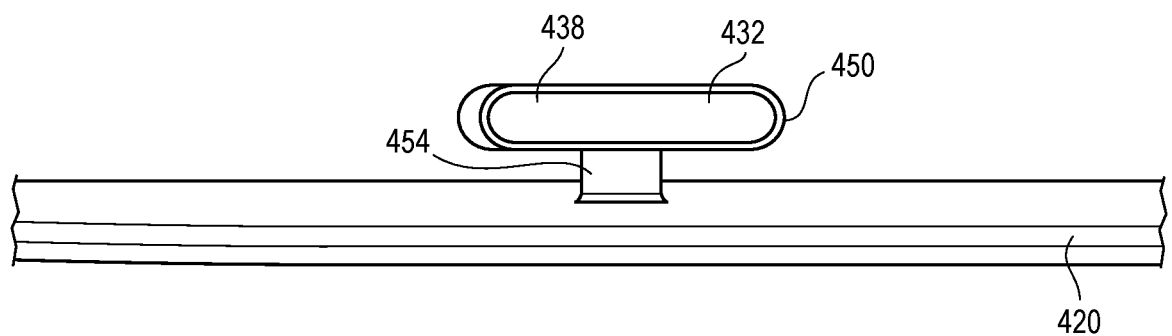
FIG. 23 is an elevational view of the retainer and the pivot member of FIG. 22.

With reference to FIG. 23, to assemble the body portion 409 and the retainer 420, an end 450 of the pivot member 432 may be raised to make the head 438 extend somewhat vertically and advanced through the opening 430 of the body portion 409. The remainder of the head 438 is then advanced into the opening 430 until the head 430 snaps into the countersunk portion 136. With the head 438 positioned in the countersunk portion 436, a shaft 454 of the pivot member 432 extends through a lower end of the opening 430.

Figure 24:
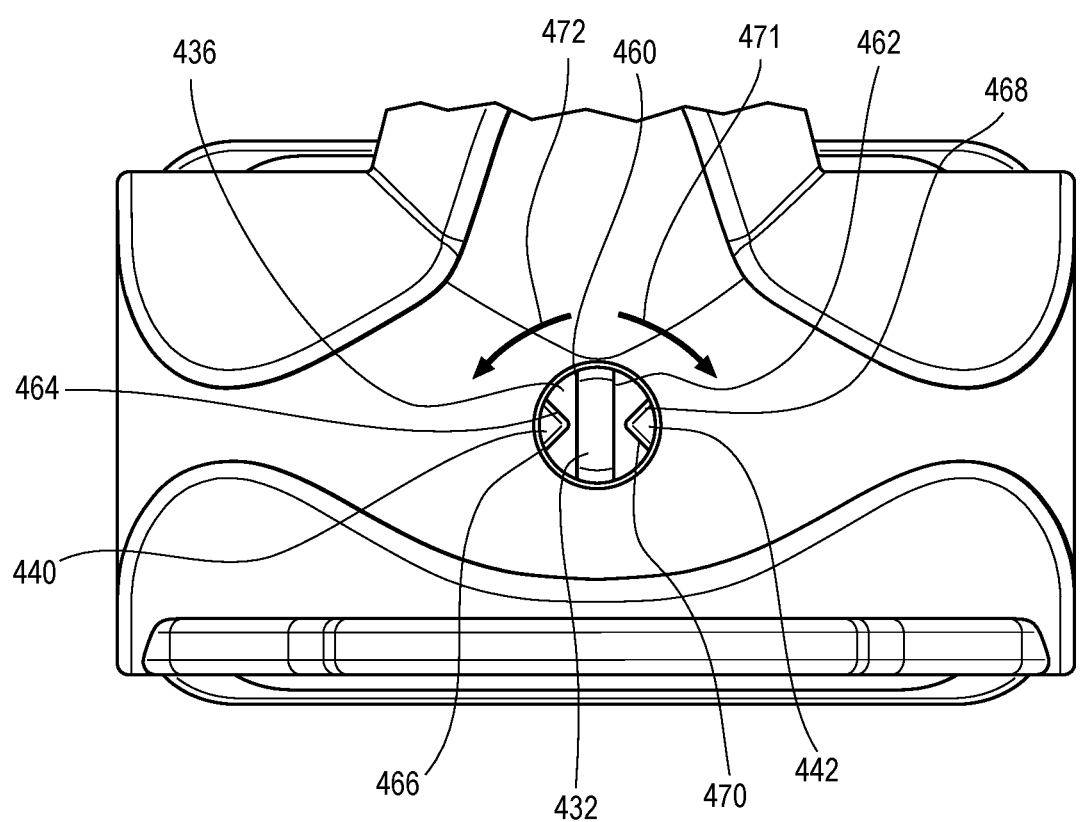
FIG. 24 is a top plan view of the securement device of FIG. 21 showing the pivot member of the retainer received in the opening of the securement device to pivotally connect the securement device and the retainer.

With reference to FIG. 24, the head 438 of the pivot member 432 includes a pair of opposite side surface 460, 462. The stops 440, 442 each have a pair of stop surfaces 464, 466 and 468, 470. The surfaces 464, 466 extend transversely to each other, such as approximately 90 degrees, and the surfaces 468, 470 also extend transversely to each other. The stops 440, 442 limit pivoting of the body portion 409 relative to the retainer 420 in the following manner. Specifically, when the body portion 409 turns in direction 471 relative to the retainer 420, the side surface 462 of the head 438 contacts the surface 468 of the stop 442 and the side surface 460 of the head 438 contacts the stop surface 466 of the stop 440. Conversely, when the body portion 409 pivots in direction 472 relative to the retainer 420, the side surface 460 of the head 438 contacts the stop surface 464 of the stop 440 and the side surface 462 of the head 438 contacts the stop surface 470 of the stop 442. In this manner, the abutting contact between the head 438 and the stops 440, 442 provides controlled pivoting of the body portion 409 relative to the retainer 420. In one form, the stops 440, 442 limit the body portion 409 to a range of pivotal movement relative to the retainer 420, such as less than 180 degrees, such as approximately 90 degrees.

Figure 25:
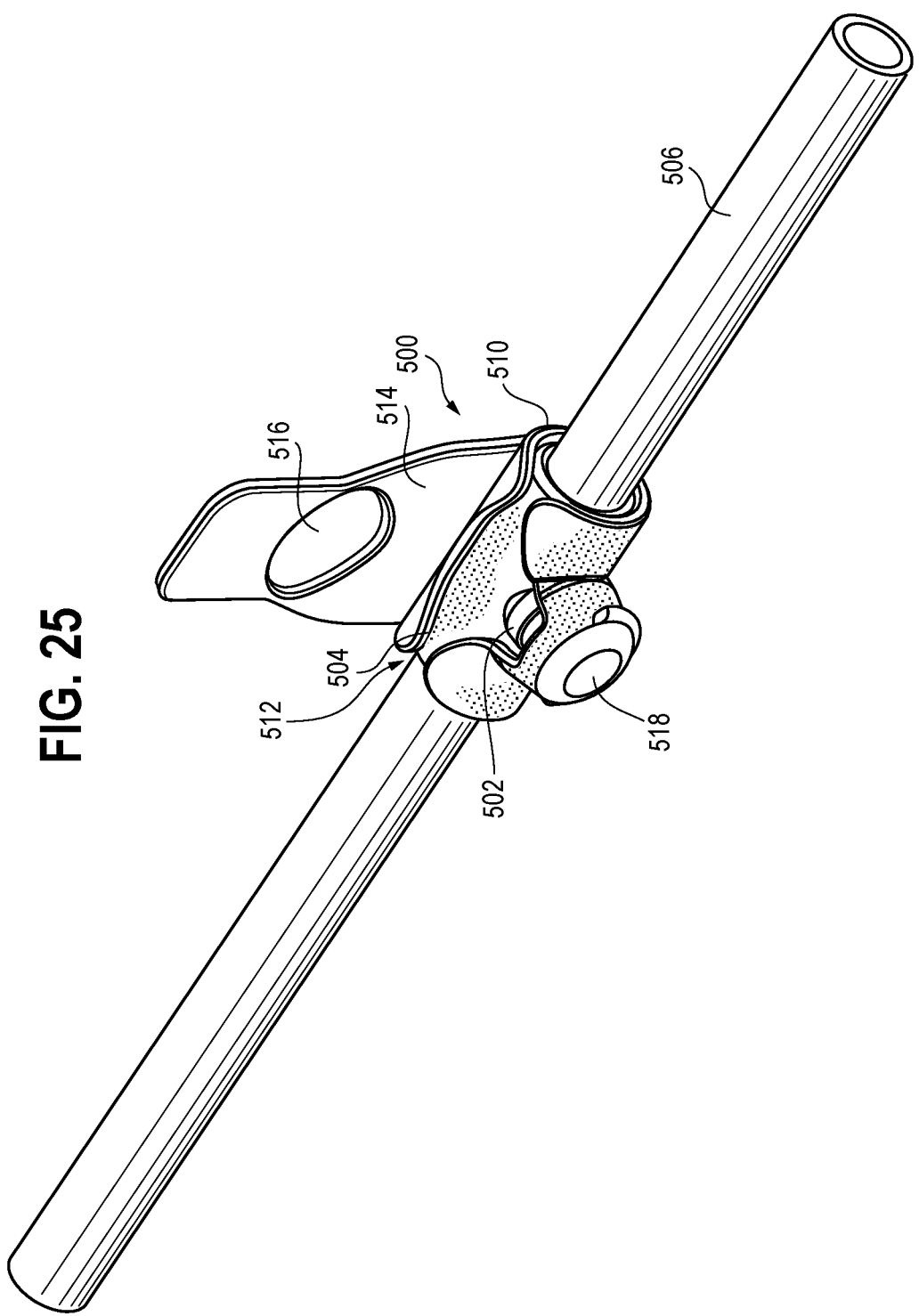
FIG. 25 is a perspective view of a securement device that protects a patient's skin from a port fitting of a catheter tube assembly by securing the luer port of the catheter tube assembly therewithin.
Figure 26:
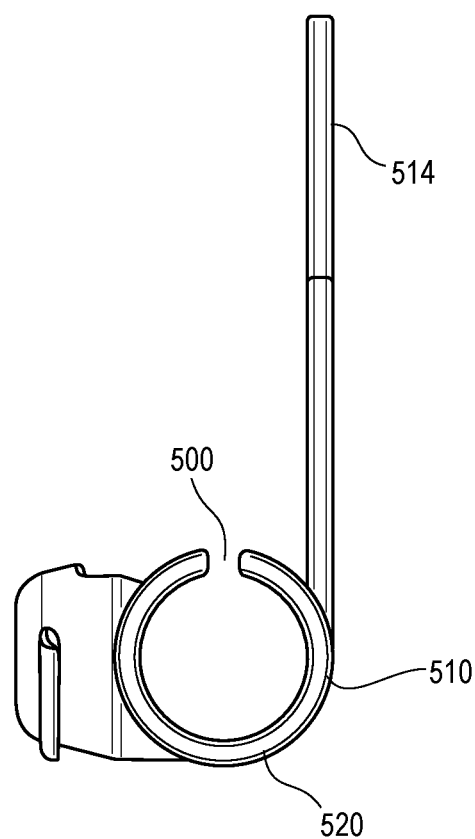
FIG. 26 is a side elevational view of the securement device of FIG. 25.

With reference to FIG. 25, a securement device 500 is provided that is similar in many respects to the securement device 203 discussed above. The securement device 500 may not include a retainer and support material and may instead primarily be used for protecting a patient's skin from a port 502 of a port fitting 504 of a catheter tubing assembly 506. The securement device 500 includes a body portion 510 with a generally tubular channel 512 that receives the port fitting 504 and a strap portion 514 with an opening 516 that is fit over a plug 518 to retain the port fitting 504 in the channel 512. With reference to FIG. 26, the body portion 510 has a rounded lower portion 520.

Figure 27:
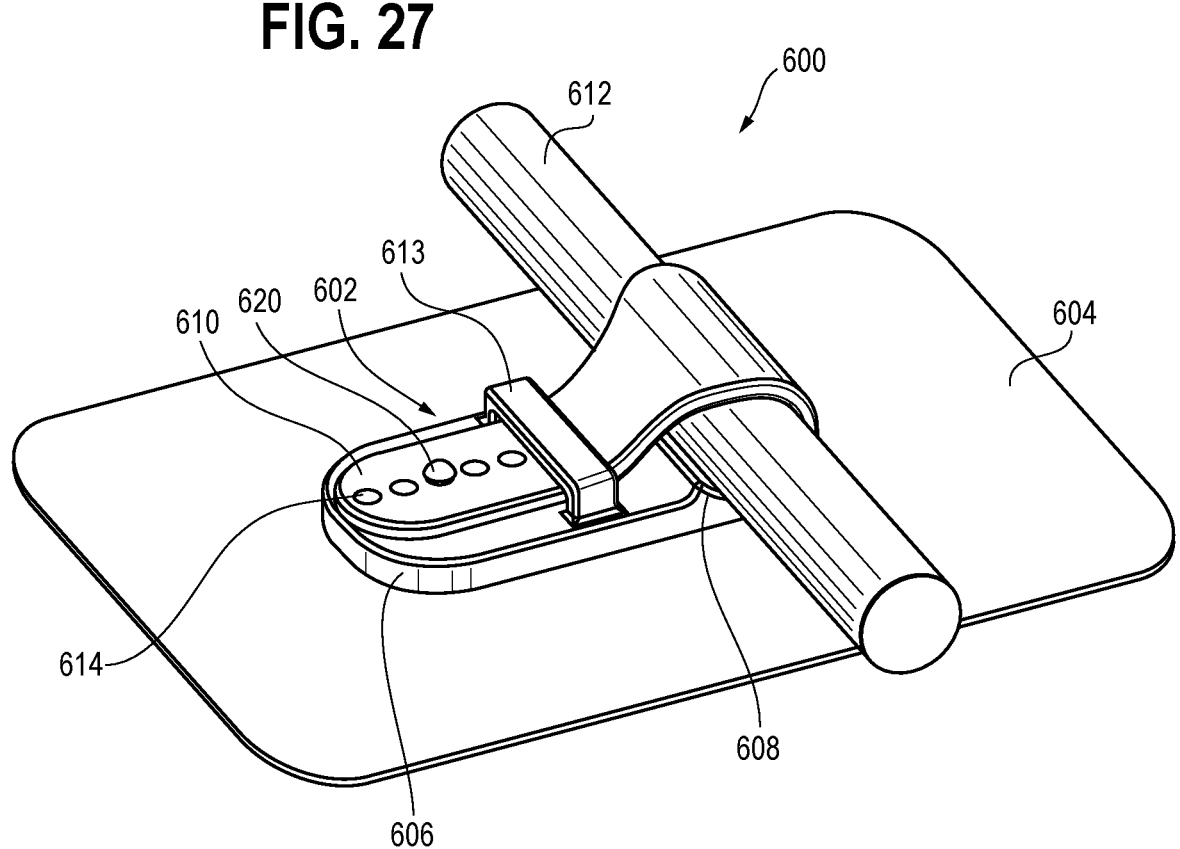
FIG. 27 is a perspective view of a strap assembly for retaining catheter tubes of various sizes.

With reference to FIG. 27, the strap assembly 600 is provided includes a strap device 602 and a support material 604. The strap device 602 includes a body portion 606 with a pocket 608 for receiving catheter tubing 612 and a strap portion 610 that may be used to releasably secure the catheter tubing 612. The strap portion 610 is pivoted around the catheter tubing 612 and fed beneath a loop 613 of the body portion 606. The strap portion 610 has one or more openings 614. In use, one of the openings 614 is fit over a plug 620 of the body portion 606 to fix the strap portion 610 in position and hold the tubing 612 in the pocket 608. The plurality of openings 614 permit the securement device 602 to be used with a variety of different diameters of tubing 612.

Figure 28:
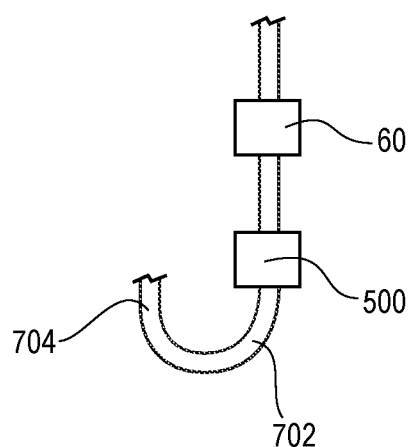
FIG. 28 is a schematic representation of a catheter system including catheter tubing and the securement device of FIG. 25 and the securement device assembly of FIG. 27.

It is generally desired to use secure a catheter tube to the inner thigh of a patient and the strap assembly is intended for use with such patients. With reference to FIG. 28, the illustrated catheter system 700 may include tubing 702 and the strap assembly 600 and the securement device 500 discussed above. The system 700 may be used for patients with shorter legs because the strap assembly 600 can be secured to the patient's inner thigh while the securement device 500 is used to cover the luer port to prevent chafing and pressure ulcers. It is thus seen that various securement devices are provided in accordance with the foregoing teachings.

Uses of singular terms such as "a," "an," are intended to cover both the singular and the plural, unless otherwise indicated herein or clearly contradicted by context. The terms "comprising," "having," "including," and "containing" are to be construed as open-ended terms. Any description of certain embodiments as "preferred" embodiments, and other recitation of embodiments, features, or ranges as being preferred, or suggestion that such are preferred, is not deemed to be limiting. The invention is deemed to encompass embodiments that are presently deemed to be less preferred and that may be described herein as such. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. A catheter securement assembly comprising:
    a securement device including:
        a body portion having an upper surface and a lower surface, the body portion having a pocket that comprises a substantially tubular channel, the channel being open at the upper surface, the body portion including a protrusion that extends from an external surface of the body portion; and
        a strap portion movable between a fully closed position and a range of open positions, the strap portion at least partially covering the pocket when in a closed position thereby closing the channel at the upper surface, the strap portion allowing access to the channel when in an open position, wherein the strap portion includes an opening extending therethrough, the opening sized to receive and engage the protrusion therein to secure the strap portion to the body portion in the fully closed position; and
    a support structure connected to the lower surface of the body portion, the support structure including:
        a retainer having an opening extending therethrough; and
        a pivot member extending through the opening of the retainer to couple the retainer and the body portion.

2. The catheter securement assembly of claim 1 wherein the body portion includes opposing side surfaces and wherein the channel is a single tubular channel that extends from one side surface to the other side surface.

3. The catheter securement assembly of claim 1 wherein the retainer is generally rectangular, the support structure further comprising:
    a support material connected to the lower surface of the body portion of the securement device, the support material having a surface area greater than a surface area of the lower surface of the body portion, the support material having a support material upper side that extends adjacent to the pivot member.

4. The catheter securement assembly of claim 1, wherein the support structure further comprises:
    a support material;
    wherein the retainer is disposed at the lower surface of the body portion of the securement device; and
    wherein the pivot member permits pivoting of the body portion relative to the support material.

5. The catheter securement assembly of claim 1, the channel having an oblong cross-section.

6. The catheter securement assembly of claim 1 wherein the opening is larger than a cross section of the protrusion such that at least a portion of the opening is spaced from the protrusion when the strap portion is in the fully closed position.

7. The catheter securement assembly of claim 1 wherein a material of the strap portion entirely surrounds the opening.

8. The catheter securement assembly of claim 1 wherein the protrusion includes an enlarged portion and a lip that extends from the enlarged portion.

9. The catheter securement assembly of claim 8 wherein the lip extends from the enlarged portion in a direction generally corresponding to a closing direction of the strap portion.

10. A catheter securement device comprising:
    a body portion having an upper surface and a lower surface, the body portion having a pocket that comprises a substantially tubular channel, the channel being open at the upper surface, the pocket further including a port cavity in communication with the channel;
    a strap portion movable between a fully closed position and a range of open positions, the strap portion at least partially covering the pocket when in a closed position thereby closing the channel at the upper surface, the strap portion allowing access to the channel when in an open position; and
    a support structure connected to the lower surface of the body portion, the support structure including:
    a support material connected to the lower surface of the body portion of the securement device, the support material having a surface area greater than a surface area of the lower surface of the body portion, the support material having a support material upper side and a support material lower side; and a retainer, the retainer having a first retainer portion disposed at the support material lower side and a second retainer portion that protrudes through the support material and that engages the securement device, the securement device and the retainer each being composed of silicone material having a Shore A durometer rating in the range of 40-80.

11. A catheter securement system comprising:
a catheter tube assembly that includes a tube structure and a fitting that includes a fluid outlet;
a securement device assembly comprising:
  a securement device having:
    a body portion with an upper surface and a lower surface, the body portion having a pocket sized to receive at least a portion of the fitting within the pocket, the pocket comprising a substantially tubular channel; and
    a strap portion movable between a fully closed position and a range of open positions, the strap portion at least partially covering the pocket when in a closed position thereby closing the channel at the upper surface, the strap portion allowing access to the channel when in an open position, the strap portion including an opening extending therethrough, the opening at least partially aligned with the fluid outlet when the strap portion is in the closed position to permit fluidic communication from within the fitting through the opening of the strap.

12. The system of claim 11 wherein the body portion includes opposing side surfaces and wherein the channel is a single tubular channel that extends from one side surface to the other side surface.

13. The system of claim 11 wherein the fluid outlet is a luer port that extends at least partially through the opening of the strap portion when the strap portion is in the closed position.

14. The system of claim 11, the channel having an oblong cross-section.

15. The system of claim 11 wherein the fluid outlet is exposed through the opening when the strap portion is in the closed position.

16. The system of claim 11 wherein the body portion includes a protrusion that extends from an external surface of the body portion, and wherein the opening of the strap portion surrounds at least a portion of the protrusion and at least a portion of the fluid outlet when the strap portion is in the closed position.

17. The system of claim 11 wherein the fluid outlet is a vent that is at least partially aligned with the opening of the strap portion when the strap portion is in the closed position.

18. The system of claim 11 further comprising a support structure, the support structure comprising:
a support material;
a retainer disposed at the lower surface of the body portion and having an opening extending therethrough; and
a pivot member extending through the opening of the retainer to pivotally connect the retainer to the body portion.

19. The system of claim 18 wherein the pivot member includes an upper pivot member and a lower pivot member that is secured to the upper pivot member.

20. The system of claim 18 wherein the pivot member includes an upper pivot member that extends at least partially within the tubular channel and a lower pivot member that extends between the retainer and the support material.

21. The system of claim 18 wherein the pivot member includes an upper pivot member having an upper planar portion that extends within the tubular channel and a lower pivot member having a lower planar portion that extends between the retainer and the support material.

22. A method comprising:
providing a catheter securement system that comprises a catheter tube assembly and a securement device assembly;
the catheter tube assembly including a tube structure and a fitting that includes a fluid outlet;
the securement device assembly comprising a securement device having:
  a body portion with an upper surface and a lower surface, the body portion including a pocket sized to receive at least a portion of the fitting within the pocket, the pocket comprising a substantially tubular channel, the body portion including a protrusion that extends from an external surface of the body portion; and
  a strap portion movable between a closed position and a range of open positions, the strap portion at least partially covering the pocket when in a closed position thereby closing the channel at the upper surface, the strap portion allowing access to the channel when in an open position, wherein the strap portion includes an opening extending therethrough; and
  a support structure connected to the lower surface of the body portion;
positioning the fitting in the pocket; and
moving the strap to the closed position, including passing the protrusion through the opening of the strap portion;
wherein in the closed position, the opening is at least partially aligned with the fluid outlet and the strap portion engages the body portion at an interface of the opening and the protrusion to retain the strap portion in the closed position.

23. The method of claim 22 including deflecting a portion of the channel of the securement device by engaging the tube structure and the channel.

24. The method of claim 22 further comprising securing the securement device assembly to the skin of a patient.

25. The method of claim 22, the channel having an oblong cross-section.

* * * * *